(12) United States Patent
Janka et al.

US008969404B2

(10) Patent No.: US 8,969,404 B2
(45) Date of Patent: *Mar. 3, 2015

(54) PURIFYING CRUDE FURAN 2,5-DICARBOXYLIC ACID BY HYDROGENATION

(71) Applicant: Eastman Chemical Company, Kingsport, TN (US)

(72) Inventors: Mesfin Ejerssa Janka, Kingsport, TN (US); Charles Edwan Sumner, Jr., Kingsport, TN (US); Shane Kipley Kirk, Church Hill, TN (US); Ashfaq Shahanawaz Shaikh, Kingsport, TN (US); Kenny Randolph Parker, Afton, TN (US)

(73) Assignee: Eastman Chemical Company, Kingsport, TN (US)

( * ) Notice: Subject to any disclaimer, the term of this patent is extended or adjusted under 35 U.S.C. 154(b) by 27 days.

This patent is subject to a terminal disclaimer.

(21) Appl. No.: 13/758,080

(22) Filed: Feb. 4, 2013

(65) Prior Publication Data

US 2013/0345452 A1  Dec. 26, 2013

Related U.S. Application Data

(60) Provisional application No. 61/663,246, filed on Jun. 22, 2012.

(51) Int. Cl.
*A61K 31/341* (2006.01)
*C07D 307/34* (2006.01)
*C07D 307/68* (2006.01)

(52) U.S. Cl.
CPC .................................. *C07D 307/68* (2013.01)
USPC ............ 514/448; 549/429; 549/485; 514/438

(58) Field of Classification Search
CPC ........................... A61K 31/341; C07D 307/34
USPC ........................... 549/429, 485; 514/438, 448
See application file for complete search history.

(56) References Cited

U.S. PATENT DOCUMENTS

| | | | |
|---|---|---|---|
| 2,797,197 | A | 6/1957 | Thompson et al. |
| 3,203,963 | A | 8/1965 | Hales et al. |
| 3,326,944 | A | 6/1967 | Lew |
| 4,977,283 | A | 12/1990 | Leupold et al. |
| 6,737,481 | B1 | 5/2004 | Kurian et al. |
| 7,052,764 | B2 | 5/2006 | Chang et al. |
| 7,385,081 | B1 | 6/2008 | Gong |
| 7,411,078 | B2 | 8/2008 | Miura et al. |
| 7,572,925 | B2 | 8/2009 | Dumesic et al. |
| 7,700,788 | B2 | 4/2010 | Lilga et al. |
| 8,183,020 | B2 | 5/2012 | Hanke |
| 8,193,381 | B2 | 6/2012 | Lilga et al. |
| 8,193,382 | B2 | 6/2012 | Lilga et al. |
| 2003/0055271 | A1 | 3/2003 | Grushin et al. |
| 2006/0205977 | A1 | 9/2006 | Sumner, Jr. et al. |
| 2007/0232815 | A1 | 10/2007 | Miura et al. |
| 2009/0124829 | A1 | 5/2009 | Gong |
| 2009/0131690 | A1 | 5/2009 | Gruter et al. |
| 2009/0156841 | A1 | 6/2009 | Sanborn et al. |
| 2009/0326262 | A1 | 12/2009 | Wan |
| 2010/0210867 | A1 | 8/2010 | Bustamante et al. |
| 2011/0092720 | A1 | 4/2011 | Yutaka et al. |

FOREIGN PATENT DOCUMENTS

| | | |
|---|---|---|
| CS | 87340 | 7/1959 |
| EP | 1 834 951 A1 | 9/2007 |
| EP | 2 197 868 B1 | 4/2011 |
| EP | 2 197 865 B1 | 8/2012 |
| JP | 2007-261986 A | 10/2007 |
| JP | 2007-261990 A | 10/2007 |
| JP | 2009-001519 A | 1/2009 |
| JP | 2009-013079 A | 1/2009 |
| JP | 2009-242312 A | 10/2009 |
| SU | 162962 A | 9/1962 |
| WO | WO 02/098836 A1 | 12/2002 |
| WO | WO 2007/092183 A2 | 8/2007 |
| WO | WO 2008/054804 A2 | 5/2008 |
| WO | WO 2009/023174 A2 | 2/2009 |
| WO | WO 2009/030506 A4 | 3/2009 |
| WO | WO 2009/030507 A4 | 3/2009 |
| WO | WO 2010/077133 A1 | 7/2010 |
| WO | WO 2010/132740 A2 | 11/2010 |

(Continued)

OTHER PUBLICATIONS

Slavinskaya, V. A., et al., "Liquid-Phase Catalytic Oxidation of 5-Methylfurfural," React. Kinet. Catal. Lett., 1979, vol. 11, No. 3, pp. 215-220.
Gandini, A., et al., "Rapid Communication: The Furan Counterpart of Poly(ethylene terephthalate): An Alternative Material Based on Renewable Resources," Journal of Polymer Science: Part A: Polymer Chemistry, 2009, vol. 47, pp. 295-298, Wiley Periodicals, Inc.
Partenheimer, W. et al., "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalysts," Adv. Synth. Catal., 2001, vol. 343, No. 1, pp. 102-111.
Lewkowski, J.; "Synthesis, Chemistry and Applications of 5-Hydroxymethylfurfural and its Derivatives," ARKIVOC, 2001, pp. 17-54.
Zakharov, I. V., "Mechanism of Initiation and Inhibition by Mn(II) in Hydrocarbon Oxidation in the Presence a Cobalt—Manganese Bromide Catalyst," Kinetics and Catalysis, 1998, vol. 39, No. 4, pp. 485-492.

(Continued)

*Primary Examiner* — Golam M M Shameem
(74) *Attorney, Agent, or Firm* — Dennis V. Carmen

(57) ABSTRACT

A process for purifying a crude furan 2,5-dicarboxylic acid composition (cFDCA) by hydrogenation of a FDCA composition dissolved in a hydrogenation solvent such as water, and hydrogenating under mild conditions, such as at a temperature within a range of 130° C. to 225° C. by contacting the solvated FDCA composition with hydrogen in the presence of a hydrogenation catalyst under a hydrogen partial pressure within a range of 10 psi to 900 psi. A product FDCA composition is produced having a low amount of tetrahydrofuran dicarboxylic acid, a low b*, and a low amount of 5-formyl furan-2-carboxylic acid (FFCA).

29 Claims, 1 Drawing Sheet

(56) References Cited

FOREIGN PATENT DOCUMENTS

WO   WO 2011/043660 A2   4/2011
WO   WO 2012/161968 A1   11/2012

OTHER PUBLICATIONS

Jiao, X. J. et al., "Kinetics of Manganese(III) Acetate in Acetic Acid: Generation of Mn(III) with Co(III), Ce(IV), and Dibromide Radicals; Reactions of Mn(III) with Mn(II), Co(II), Hydrogen Bromide, and Alkali Bromides," Inorg. Chem., 2000, vol. 39, pp. 1549-1554, American Chemical Society.
Copending U.S. Appl. No. 13/228,816, filed Sep. 9, 2011, Mesfin Ejerssa Janka, et al.
Copending U.S. Appl. No. 13/228,799, filed Sep. 9, 2011, Mesfin Ejerssa Janka, et al.
Copending U.S. Appl. No. 13/228,809, filed Sep. 9, 2011, Mesfin Ejerssa Janka, et al.
Copending U.S. Appl. No. 13/228,803, filed Sep. 9, 2011, Mesfin Ejerssa Janka, et al.
Copending U.S. Appl. No. 13/228,797, filed Sep. 9, 2011, Mesfin Ejerssa Janka, et al.
Copending U.S. Appl. No. 13/228,813, filed Sep. 9, 2011, Ashfaq Shaikh, et al.
PCT International Search Report and Written Opinion dated Jul. 27, 2012 for International Application No. PCT/US2012/037223.
PCT International Search Report and Written Opinion dated Aug. 7, 2012 for International Application No. PCT/US2012/037218.
PCT International Search Report and Written Opinion dated Jul. 27, 2012 for International Application No. PCT/US2012/037204.
PCT International Search Report and Written Opinion dated Jul. 27, 2012 for International Application No. PCT/US2012/037206.
PCT International Search Report and Written Opinion dated Aug. 3, 2012 for International Application No. PCT/US2012/037210.
Copending U.S. Appl. No. 13/553,976, filed Jul. 20, 2012, Mesfin Ejerssa Janka, et al.
PCT International Search Report and Written Opinion dated Aug. 23, 2012 for International Application No. PCT/US2012/037228.
Chheda et al., "Production of 5-hydromethylfurfural and furfural by dehydration of biomass-derived mono- and poly-saccharides." Green Chemistry, vol. 9, pp. 342-350 (2007).
Werpy et al., "Top Value Added Chemicals from Biomass" DOE (Pacific NW National Laboratory) (Aug. 2004).
Verevkin et al., "Biomass-Derived Platform Chemicals: Thermodynamic Studies on the Conversion of 5-Hydroxymethylfurfural into Bulk Intermediates" Ind. Eng. Chem. Res., vol. 48, pp. 10087-10093 (2009).
Rodivilova et al., "Synthesis and Investigation of Polyarylates Based on 2,5-Furandicarboxylic Acid and Diphenylolpropane", Khimiya I Khimicheskaya Tekhnologiya, No. 7, 1968, pp. 818-821.
Copending U.S. Appl. No. 13/758,070, filed Feb. 4, 2013, Ashfaq Shahanawaz Shaikh, et al.
Copending U.S. Appl. No. 13/758,088, filed Feb. 4, 2013, Mesfin Ejerssa Janka, et al.
Copending U.S. Appl. No. 13/758,072, filed Feb. 4, 2014, Mesfin Ejerssa Janka, et al.
Copending U.S. Appl. No. 13/798,257, filed Mar. 13, 2013, Ashfaq Shahanawaz Shaikh.
Copending U.S. Appl. No. 13/798,235, filed Mar. 13, 2013, Ashfaq Shahanawaz Shaikh.
Office Action dated Apr. 18, 2013 received in co-pending U.S. Appl. No. 13/228,797.
Office Action dated Apr. 18, 2013 received in co-pending U.S. Appl. No. 13/228,813.
Office Action dated Apr. 29, 2013 received in co-pending U.S. Appl. No. 13/228,799.
PCT International Search Report and Written Opinion dated Oct. 31, 2013 for International Application No. PCT/US2013/050799.
Office Action dated Nov. 8, 2013 received in co-pending U.S. Appl. No. 13/228,803.
Office Action dated Nov. 12, 2103 received in co-pending U.S. Appl. No. 13/228,799.
Office Action dated Nov. 14, 2013 received in co-pending U.S. Appl. No. 13/228,809.
Office Action dated Nov. 18, 2013 received in co-pending U.S. Appl. No. 13/758,088.
Copending U.S. Appl. No. 14/084,165, filed Nov. 19, 2013, Ashfaq Shaikh et al.
PCT International Search Report and Written Opinion dated Nov. 28, 2013 for International Application No. PCT/US2013/050794.
Office Action dated Dec. 13, 2013 received in co-pending U.S. Appl. No. 13/228,816.
Office Action dated Dec. 16, 2013 received in co-pending U.S. Appl. No. 13/553,976.
Manasek, Z., "Modification of a Fiber-Forming Polyester Based on 2,5-Furandicarboxylic Acid", Mar. 20, 1963, pp. 35-38.
Office Action dated May 31, 2013 received in co-pending U.S. Appl. No. 13/228,803.
Office Action dated Jun. 6, 2013 received in co-pending U.S. Appl. No. 13/228,809.
Office Action dated Jun. 6, 2013 received in co-pending U.S. Appl. No. 13/228,816.
PCT International Search Report and Written Opinion dated Jul. 29, 2013 for International Application No. PCT/US2013/044935.
PCT International Search Report and Written Opinion dated Aug. 9, 2013 for International Application No. PCT/US2013/044932.
Office Action dated Sep. 30, 2013 received in co-pending U.S. Appl. No. 13/758,070.
Moldenhauer, et al., "Beitrage zur Furanchemie I", Justus Liebigs Annalen Der Chemie, vol. 580, 1953, pp. 169-190.
Office Action dated Oct. 25, 2013 received in co-pending U.S. Appl. No. 13/228,813.
Office Action dated Nov. 5, 2013 received in co-pending U.S. Appl. No. 13/228,797.
Office Action dated Nov. 8, 2013 received in co-pending U.S. Appl. No. 13/758,070.
Copending U.S. Appl. No. 14/259,754, filed Apr. 23, 2014, Ashfaq Shaikh et al.
Notice of Allowance dated May 13, 2014 received in co-pending U.S. Appl. No. 13/758,088.
Copending U.S. Appl. No. 14/282,360, filed May 20, 2014, Janka et al.
Office Action dated Apr. 25, 2014 received in co-pending U.S. Appl. No. 13/228,797.
Office Action dated Apr. 25, 2014 received in co-pending U.S. Appl. No. 13/228,809.
Notice of Allowance dated Apr. 28, 2014 received in co-pending U.S. Appl. No. 13/228,803.
Notice of Allowance dated Apr. 28, 2014 received in co-pending U.S. Appl. No. 13/228,813.
Office Action dated April 30, 2014 received in co-pending U.S. Appl. No. 13/798,235.
Notice of Allowance dated May 1, 2014 received in co-pending U.S. Appl. No. 13/228,799.
Office Action dated May 29, 2014 received in co-pending U.S. Appl. No. 13/228,816.
Notice of Allowance dated Jun. 11, 2014 received in co-pending U.S. Appl. No. 13/553,976.
Copending U.S. Appl. No. 14/309,010, filed Jun. 19, 2014, Janka et al.
Copending U.S. Appl. No. 14/317,588, filed Jun. 27, 2014, Parker et al.
Copending U.S. Appl. No. 14/317,692, filed Jun. 27, 2014, Janka et al.
Copending U.S. Appl. No. 14/317,782, filed Jun. 27, 2014, Parker et al.
Copending U.S. Appl. No. 14/317,875, filed Jun. 27, 2014, Janka et al.
USPTO Notice of Allowance dated Apr. 1, 2014 for co-pending U.S. Appl. No. 13/758,070.
USPTO Office Action dated Apr. 17, 2014 for co-pending U.S. Appl. No. 13/758,072.

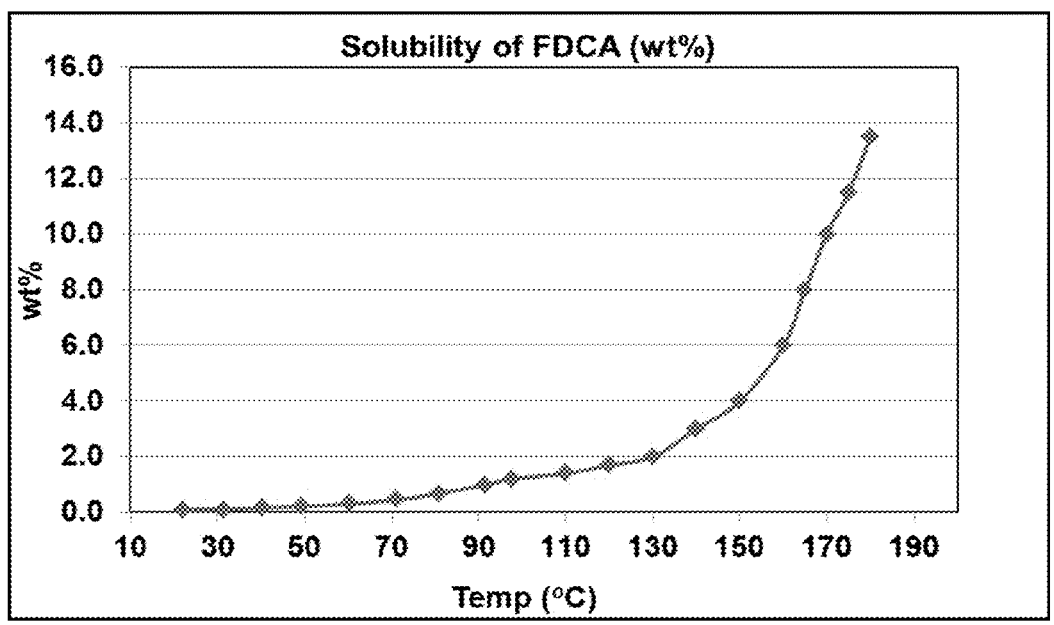

PURIFYING CRUDE FURAN 2,5-DICARBOXYLIC ACID BY HYDROGENATION

CROSS-REFERENCE TO RELATED APPLICATIONS

This application claims the priority to U.S. Provisional Patent Application No. 61/663,246, filed on 22 Jun. 2012, the entire disclosure of which is incorporated herein by reference.

FIELD OF THE INVENTION

This invention relates generally to the production of purified furan 2,5-dicarboxylic acids. In particular, the invention relates to purification of crude furan 2,5-dicarboxylic acid by mild hydrogenation.

BACKGROUND OF THE INVENTION

Aromatic dicarboxylic acids such as terephthalic acid and isophthalic acid are used to produce a variety of polyester products, important examples of which are poly(ethylene terephthalate) and its copolymers. These aromatic dicarboxylic acids are synthesized by the catalyzed autoxidation of the corresponding dialkyl aromatic compounds which are obtained from fossil fuels (US 2006/0205977 A1). There is a growing interest in the use of renewable resources as feed stocks for the chemical industries mainly due to the progressive reduction of fossil reserves and their related environmental impacts.

Furan 2,5-dicarboxylic acid ("FDCA") is a versatile intermediate considered as a promising closest biobased alternative to terephthalic acid and isophthalic acid. It is synthesized by the catalytic oxidation of 5-(hydroxymethyl)furfural (5-HMF) as shown in equation 1 below; or by the catalytic oxidation of 5-HMF esters (5-R(CO)OCH$_2$-furfural where R=alkyl, cycloalkyl and aryl) as shown in equation 2 below; or by the catalytic oxidation of 5-HMF ethers (5-R'OCH$_2$-furfural, where R'=alkyl, cycloalkyl and aryl) as shown in equation 3 below; or by the catalytic oxidation of 5-alkyl furfurals (5-R"-furfural, where R"=alkyl, cycloalkyl and aryl) as shown in equation 4 below; in each case using a Co/Mn/Br catalyst system. Mixed feedstocks of 5-HMF and 5-HMF esters, mixed feedstocks of 5-HMF and 5-HMF ethers, and mixed feedstocks of 5-HMF and 5-alkyl furfurals can also be used.

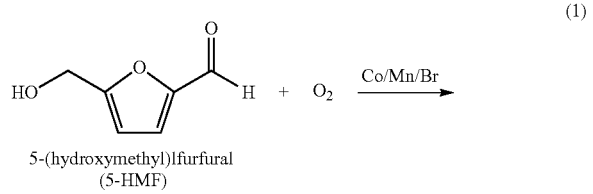

(1)

5-(hydroxymethyl)furfural (5-HMF)

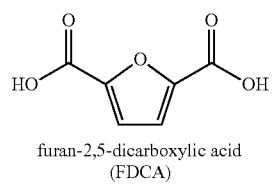

furan-2,5-dicarboxylic acid (FDCA)

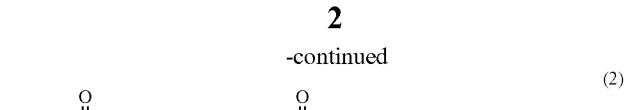

5-(acetoxymethyl)furfural (5-AMF)

(FDCA)

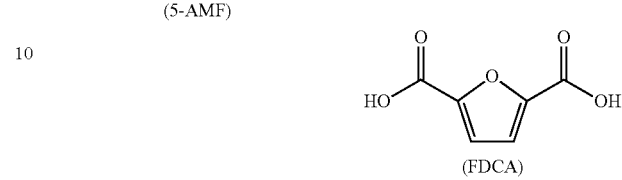

5-(ethoxymethyl)furfural (5-EMF)

(FDCA) +

5-(ethoxycarbonyl)furan-2-carboxylic acid (EFCA)

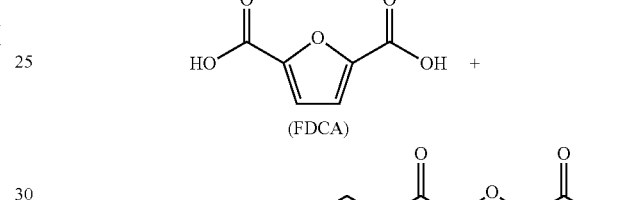

5-(methyl)furfural (5-MF)

(FDCA)

We have found that the above reactions work well. However a number of impurities are produced, particularly mono-carboxylic acid species such as 5-formyl furan-2-carboxylic acid (FFCA). These mono-carboxylic acids are not desirable since they terminate the chain growth of a polymer resulting in lower polymer viscosity. If colored bodies are present in the crude FDCA or remaining in the product FDCA, these colored bodies carry through to compounds or polymers using the FDCA as a reactive monomer to thereby color the compound or polymer. Therefore, it is necessary to purify the crude FDCA to remove the color bodies while minimizing the presence of FFCA in the product FDCA.

In process for the manufacture of terephthalic acid, one conventional method of purifying crude terephthalic acid (CTA) is to produce purified terephthalic acid (PTA) is by subjecting the CTA to a hydrogenation treatment, where 4-CBA (a chain terminator) is hydrogenated to para-toluic acid and color bodies are hydrogenated to colorless solid compounds. To accomplish purification by hydrogenation, solid CTA particles are typically dissolved in a solvent (e.g., water), and the resulting solution is subjected to liquid-phase hydrogenation in the presence of a hydrogenation catalyst. Although effective to reduce yellowness, purification of CTA by hydrogenation can be expensive because it is conducted under high reaction temperatures thereby consuming a large amount of energy and conducted under high hydrogen partial pressure thereby consuming a large amount of hydrogen.

Thus, there remains a need to effectively reduce the color bodies in crude FDCA without consuming large amount of energy or hydrogen in the process.

SUMMARY OF THE INVENTION

In this invention we disclose a process to make a product FDCA (pFDCA) that has been purified by catalytic hydrogenation under mild conditions.

In particular there is now provided a process for purifying a crude furan 2,5-dicarboxylic acid composition (cFDCA) comprising:
 a) providing a cFDCA composition comprising furan 2,5-dicarboxylic acid (FDCA) solids, 5-formyl furan-2-carboxylc acid (FFCA), and a oxidation solvent composition;
 b) combining a hydrogenation solvent composition with said FDCA solids and dissolving at least a portion of the FDCA solids to thereby produce a solvated FDCA (sFDCA) composition comprising dissolved FDCA, the hydrogenation solvent composition, and FFCA;
 c) in a hydrogenation reaction zone, hydrogenating the sFDCA at a temperature within a range of 130° C. to 225° C. by contacting the sFDCA composition with hydrogen in the presence of a hydrogenation catalyst to thereby hydrogenate FFCA and produce a furan 2,5-dicarboxylic acid composition (hFDCA) comprising a hydrogenated FFCA species, dissolved FDCA, and said hydrogenation solvent; and
 e) separating at least a portion of the dissolved FDCA from the hFDCA composition to obtain a product FDCA (pFDCA) composition.

Desirably, a pFDCA composition is provided that has been purified by hydrogenation at a temperature within a range of 130° C. to 225° C. by contacting the sFDCA composition with hydrogen in the presence of a hydrogenation catalyst under a hydrogen partial pressure within a range of 10 psi to 900 psi.

BRIEF DESCRIPTION OF THE DRAWINGS

FIG. 1 depicts the solubility of FDCA in water at different temperatures.

DETAILED DESCRIPTION OF THE INVENTION

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," "contain," "including," "includes," "include," and "have" have the same open-ended meaning as "comprising," "comprises," and "comprise" provided above.

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds) and provided literal support for and includes the end points of 10 and 100.

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. For example, if the specification describes a specific temperature of 62° F., such a description provides literal support for a broad numerical range of 25° F. to 99° F. (62° F.+/−37° F.), an intermediate numerical range of 43° F. to 81° F. (62° F.+/−19° F.), and a narrow numerical range of 53° F. to 71° F. (62° F.+/−9° F.). These broad, intermediate, and narrow numerical ranges should be applied not only to the specific values, but should also be applied to differences between these specific values. Thus, if the specification describes a first pressure of 110 psia and a second pressure of 48 psia (a difference of 62 psi), the broad, intermediate, and narrow ranges for the pressure difference between these two streams would be 25 to 99 psi, 43 to 81 psi, and 53 to 71 psi, respectively All amounts are by weight unless otherwise specified. All amounts by weight are based on the weight of the whole composition stream containing the ingredient in question rather than a part of that composition or a different stream altogether, unless otherwise noted. All stated amounts in ppm are by weight (ppmw) unless otherwise noted.

There is provided a crude FDCA (cFDCA) composition comprising furan 2,5-dicarboxylic acid (FDCA) solids, 5-formyl furan-2-carboxylc acid (FFCA), and a oxidation solvent composition. This composition may be provided in a variety of ways. One technique is described as follows.

An oxidizable composition is fed to an oxidation zone, where the oxidizable composition contains a compound having a furan moiety. The furan moiety can be represented by the structure:

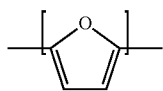

The compounds having a furan moiety are such that, upon oxidation, form carboxylic acid functional groups on the compound. Examples of compounds having furan moieties include 5-(hydroxymethyl)furfural (5-HMF), and derivatives of 5-HMF. Such derivatives include esters of 5-HMF, such as those represented by the formula 5-R(CO)OCH$_2$-furfural where R=alkyl, cycloalkyl and aryl groups having from 1 to 8 carbon atoms, or 1-4 carbon atoms or 1-2 carbon atoms; ethers of 5-HMF represented by the formula 5-R'OCH$_2$-furfural, where R'=alkyl, cycloalkyl and aryl having from 1 to 8 carbon atoms, or 1-4 carbon atoms or 1-2 carbon atoms); 5-alkyl furfurals represented by the formula 5-R"-furfural, where R"=alkyl, cycloalkyl and aryl having from 1 to 8 carbon atoms, or 1-4 carbon atoms or 1-2 carbon atoms). Thus the oxidizable composition can contain mixtures of 5-HMF and 5-HMF esters; 5-HMF and 5-HMF ethers; 5-HMF and 5-alkyl furfurals, or mixtures of 5-HMF and its esters, ethers, and alkyl derivatives.

The oxidizable composition, in addition to 5-(hydroxymethyl)furfural (5-HMF) or an of its derivatives, may also contain 5-(acetoxymethyl)furfural (5-AMF) and 5-(ethoxymethyl)furfural (5-EMF).

Specific examples of 5-HMF derivatives include those having the following structures:

Preferred 5-HMF Derivative Feeds

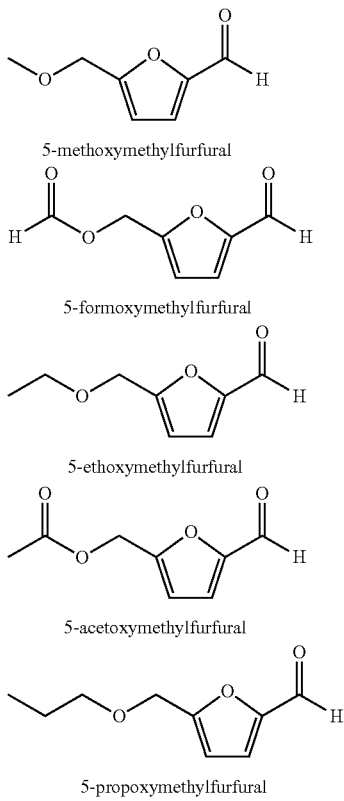

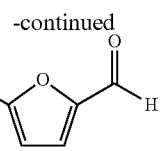

5-propionoxymethylfurfural

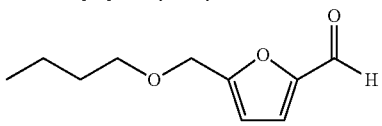

5-butoxymethylfurfural

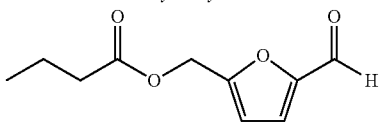

5-butyroxymethylfurfural

An oxidizable composition is fed to a primary oxidation zone and reacted in the presence of a oxidation solvent composition, a catalyst system, and a gas comprising oxygen, to generate a crude dicarboxylic acid stream comprising furan-2,5-dicarboxylic acid (FDCA).

For example, the oxidizable composition containing 5-HMF, or its derivatives, or combinations thereof, are oxidized with O$_2$ in a multi-step reaction to form FDCA with 5-formyl furan-2-carboxylic acid (FFCA) as a key intermediate, represented by the following sequence:

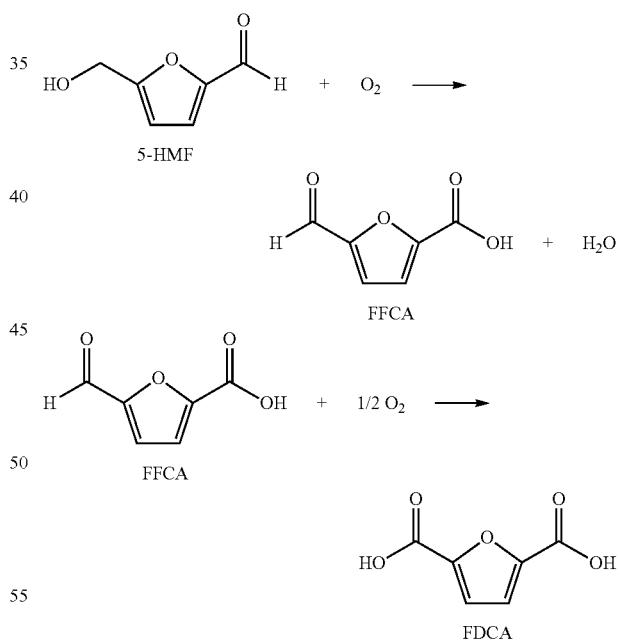

If desired, the oxygen gas stream comprising oxygen, an oxidation solvent composition stream, and the oxidizable stream can be fed to a primary oxidation zone as separate streams. Or, an oxygen stream comprising oxygen as one stream and an oxidizable stream comprising oxidation solvent composition, catalyst, and oxidizable compounds as a second stream can be fed to the primary oxidation zone. Accordingly, the oxidation solvent composition, oxygen gas comprising oxygen, catalyst system, and oxidizable compounds can be fed to the primary oxidization zone as separate and individual streams or combined in any combination prior to entering the primary oxidization zone wherein these feed streams may enter at a single location or in multiple locations into the primary oxidizer zone.

The catalyst can be a homogenous catalyst soluble in the oxidation solvent composition or a heterogeneous catalyst. The catalyst composition is desirably soluble in the oxidation solvent composition under reaction conditions, or it is soluble in the reactants fed to the oxidation zone. Preferably, the catalyst composition is soluble in the oxidation solvent composition at 40° C. and 1 atm, and is soluble in the oxidation solvent composition under the reaction conditions.

Suitable catalysts components comprise at least one selected from, but are not limited to, cobalt, bromine and manganese compounds. Preferably a homogeneous catalyst system is selected. The preferred catalyst system comprises cobalt, manganese and bromine.

The cobalt atoms may be provided in ionic form as inorganic cobalt salts, such as cobalt bromide, cobalt nitrate, or cobalt chloride, or organic cobalt compounds such as cobalt salts of aliphatic or aromatic acids having 2-22 carbon atoms, including cobalt acetate, cobalt octanoate, cobalt benzoate, cobalt acetylacetonate, and cobalt naphthalate. The oxidation state of cobalt when added as a compound to the reaction mixture is not limited, and includes both the +2 and +3 oxidation states.

The manganese atoms may be provided as one or more inorganic manganese salts, such as manganese borates, manganese halides, manganese nitrates, or organometallic manganese compounds such as the manganese salts of lower aliphatic carboxylic acids, including manganese acetate, and manganese salts of beta-diketonates, including manganese acetylacetonate.

The bromine component may be added as elemental bromine, in combined form, or as an anion. Suitable sources of bromine include hydrobromic acid, sodium bromide, ammonium bromide, potassium bromide, and tetrabromoethane. Hydrobromic acid or sodium bromide may be preferred bromine sources.

The amount of bromine atoms desirably ranges from at least 300 ppm, or at least 2000 ppm, or at least 2500 ppm, or at least 3000 ppm, or at least 3500 ppm, or at least 3750, ppm and up to 4500 ppm, or up to 4000 ppm, based on the weight of the liquid in the reaction medium of the primary oxidation zone. Bromine present in the amount of 2500 ppm to 4000 ppm, or 3000 ppm to 4000 ppm are especially desirable to promote high yield.

The amount of cobalt atoms can range from at least 500 ppm, or at least 1500 ppm, or at least 2000 ppm, or at least 2500 ppm, or at least 3000 ppm, and up to 6000 ppm, or up to 5500 ppm, or up to 5000 ppm, based on the weight of the liquid in the reaction medium of the primary oxidation zone. Cobalt present in an amount of 2000 ppm to 6000 ppm, or 2000 ppm to 5000 ppm is especially desirable to promote high yield.

The amount of manganese atoms can range from 2 ppm, or at least 10 ppm, or at least 30 ppm, or at least 50 ppm, or at least 70 ppm, or at least 100 ppm, and in each case up to 600 ppm, or up to 500 ppm or up to 400 ppm, or up to 350 ppm, or up to 300 ppm, or up to 250 ppm, based on the weight of the liquid in the reaction medium of the primary oxidation zone. Manganese present in an amount ranging from 30 ppm to 400 ppm, or 70 ppm to 350 ppm, or 100 ppm to 350 ppm is especially desirable to promote high yield.

The weight ratio of cobalt atoms to manganese atoms in the reaction mixture can be from 1:1 to 400:1 or 10:1 to about 400:1. A catalyst system with improved Co:Mn ratio can lead to high yield of FDCA. To increase the yield of FDCA, when the oxidizable composition fed to the oxidation reactor comprises 5-HMF, then the cobalt to manganese weight ratio is at least 10:1, or at least 15:1, or at least 20:1, or at least 25:1, or at least 30:1, or at least 40:1 or at least 50:1, or at least 60:1, and in each case up to 400:1. However, in the case where the oxidizable composition comprises esters of 5-HMF, ethers of 5-HMF, or 5-alkyl furfurals, or mixtures of any of these compounds together or with 5-HMF, the cobalt to manganese weight ratio can be lowered while still obtaining high yield of FDCA, such as a weight ratio of Co:Mn of at least 1:1, or at least 2:1, or at least 5:1, or at least 9:1, or at least 10:1, or at least 15:1, or at least 20:1, or at least 25:1, or at least 30:1, or at least 40:1, or at least 50:1, or at least 60:1 and in each case up to 400:1.

The weight ratio of cobalt atoms to bromine atoms is desirably at least 0.7:1, or at least 0.8:1, or at least 0.9:1, or at least 1:1, or at least 1.05:1, or at least 1.2:1, or at least 1.5:1, or at least 1.8:1, or at least 2:1, or at least 2.2:1, or at least 2.4:1, or at least 2.6:1, or at least 2.8:1, and in each case up to 3.5, or up to 3.0, or up to 2.8.

The weight ratio of bromine atoms to manganese atoms is from about 2:1 to 500:1.

Desirably, the weight ratio of cobalt to manganese is from 10:1 to 400:1, and the weight ratio of cobalt to bromine atoms ranges from 0.7:1 to 3.5:1. Such a catalyst system with improved Co:Mn and Co:Br ratio can lead to high yield of FDCA (minimum of 90%), decrease in the formation of impurities (measured by b*) causing color in the downstream polymerization process while keeping the amount of CO and $CO_2$ (carbon burn) in the off-gas at a minimum.

Desirably, the amount of bromine present is at least 1000 ppm and up to 3500 ppm, and the weight ratio of bromine to manganese is from 2:1 to 500:1. This combination has the advantage of high yield and low carbon burn.

Desirably, the amount of bromine present is at least 1000 ppm and up to 3000 ppm, and the amount of cobalt present is at least 1000 ppm and up to 3000 ppm, and the weight ratio of cobalt to manganese is from 10:1 to 100:1. This combination has the advantage of high yield and low carbon burn.

Suitable oxidation solvent compositions include aliphatic oxidation solvent compositions. In an embodiment of the invention, the oxidation solvent compositions are aliphatic carboxylic acids which include, but are not limited to, $C_2$ to $C_6$ monocarboxylic acids, e.g., acetic acid, propionic acid, n-butyric acid, isobutyric acid, n-valeric acid, trimethylacetic acid, caprioic acid, and mixtures thereof.

The most common oxidation solvent composition used for the oxidation is an aqueous acetic acid solution, typically having an acetic acid concentration of 80 to 99 wt. % before adding it to the oxidation zone. In especially preferred embodiments, the oxidation solvent composition as added comprises a mixture of water and acetic acid which has a water content of 0% to about 15% by weight. Additionally, a portion of the oxidation solvent composition feed to the primary oxidation reactor may be obtained from a recycle stream obtained by displacing about 80 to 90% of the mother liquor taken from the crude reaction mixture stream discharged from the primary oxidation reactor with fresh, wet acetic acid containing about 0 to 15% water.

The oxidizing gas stream comprises oxygen. Examples include, but are not limited to, air and purified oxygen. The amount of oxygen in the primary oxidation zone ranges from about 5 mole % to 45 mole %, 5 mole % to 60 mole %, 5 mole % to 80 mole %.

The temperature of the reaction mixture in the primary oxidation zone can vary from about 100° C. to about 220° C. The temperature of the reaction mixture in the primary oxidation zone is at least 100° C., or at least 105° C., or at least 110° C., or at least 115° C., or at least 120° C., or at least 125° C., or at least 130° C., or at least 135° C., or at least 140° C., or at least 145° C., or at least 150° C., or at least 155° C., or at least 160° C., and can be as high as 220° C., or up to 210° C., or up to 200° C., or up to 195° C., or up to 190° C., or up to 180° C., or up to 175° C., or up to 170° C., or up to 165° C., or up to 160° C., or up to 155° C., or up to 150° C., or up to 145° C., or up to 140° C., or up to 135° C., or up to 130° C. In other embodiments, the temperate ranges from 105° C. to 180° C., or from 105° C. to 175° C., or from 105° C. to 170° C., or from 105° C. to 165° C., or from 105° C. to 160° C., or from 105° C. to 155° C., or from 105° C. to 150° C., or from 110° C. to 180° C., or from 110° C. to 175° C., or from 110° C. to 170° C., or from 110° C. to 165° C., or from 110° C. to 160° C., or from 110° C. to 155° C., or from 110° C. to 150° C., or from 110° C. to 145° C., or from 115° C. to 180° C., or from 115° C. to 175° C., or from 115° C. to 170° C., or from 115° C. to 165° C., or from 115° C. to 160° C., or from 115° C. to 155° C., or from 110° C. to 150° C., or from 115° C. to 145° C., or from 120° C. to 180° C., or from 120° C. to 175° C., or from 120° C. to 170° C., or from 120° C. to 165° C., or from 120° C. to 160° C., or from 120° C. to 155° C., or from 120° C. to 150° C., or from 120° C. to 145° C., or from 125° C. to 180° C., or from 125° C. to 175° C., or from 125° C. to 170° C., or from 125° C. to 165° C., or from 125° C. to 160° C., or from 125° C. to 155° C., or from 125° C. to 150° C., or from 125° C. to 145° C., or from 130° C. to 180° C., or from 130° C. to 175° C., or from 130° C. to 170° C., or from 130° C. to 165° C., or from 130° C. to 160° C., or from 130° C. to 155° C., or from 130° C. to 150° C., or from 130° C. to 145° C., or from 135° C. to 180° C., or from 135° C. to 175° C., or from 135° C. to 170° C., or from 135° C. to 165° C., or from 135° C. to 160° C., or from 135° C. to 155° C., or from 135° C. to 150° C., or from 135° C. to 145° C., or from 140° C. to 180° C., or from 140° C. to 175° C., or from 140° C. to 170° C., or from 140° C. to 170° C., or from 140° C. to 165° C., or from 140° C. to 160° C., or from 140° C. to 155° C., or from 140° C. to 150° C., or from 140° C. to 145° C., or from 145° C. to 180° C., or from 145° C. to 175° C., or from 145° C. to 170° C., or from 145° C. to 170° C., or from 145° C. to 165° C., or from 145° C. to 160° C., or from 145° C. to 155° C., or from 145° C. to 150° C., or from 150° C. to 180° C., or from 150° C. to 175° C., or from 150° C. to 170° C., or from 150° C. to 165° C., or from 150° C. to 160° C., or from 150° C. to 155° C., or from 155° C. to 180° C., or from 155° C. to 175° C., or from 155° C. to 170° C., or from 155° C. to 165° C., or from 155° C. to 160° C., or from 160° C. to 180° C., or from 160° C. to 175° C., or from 160° C. to 170° C., or from 160° C. to 165° C., or from 165° C. to 180° C., or from 165° C. to 175° C., or from 165° C. to 170° C., or from 165° C. to 180° C., or from 165° C. to 175° C., or from 165° C. to 170° C., or from 170° C. to 180° C., or from 170° C. to 175° C., or from 175° C. to 180° C.

To minimize carbon burn, it is desired that the temperature of the reaction mixture is not greater than 165° C., or not greater than 160° C. The contents of the oxidizer off gas comprise COx, wherein x is 1 or 2, and the amount of COx in the oxidizer off gas is less than 0.05 moles of COx per mole of the total oxidizable feed to the reaction medium, or no more than 4 moles of COx per mole of the total oxidizable feed to the reaction medium, or no more than 6 moles of COx per mole of the total oxidizable feed to the reaction medium. The carbon burn as determined by the COx generation rate can be calculated as follows: (moles of CO+moles of CO2)/moles of oxidizable feed. The low carbon burn generation rate is achievable by the combination of low reaction temperature, and the molar weight ratios of the catalyst components as described above.

The oxidation reaction can be conducted under a pressure ranging from 40 to 300 psia. A bubble column is desirably operated under a pressure ranging from 40 psia to 150 psia. In a stirred tank vessel, the pressure is desirably set to 100 psia to 300 psia.

Oxidizer off gas stream containing COx (CO and $CO_2$), water, nitrogen, and vaporized oxidation solvent composition, is routed to the oxidizer off gas treatment zone to generate an inert gas stream, liquid stream comprising water, and a recovered oxidation solvent composition stream comprising condensed oxidation solvent composition. In one embodiment, the oxidizer off gas stream can be fed to directly, or indirectly after separating condensables such as oxidation solvent composition from non-condensables such as COx and nitrogen in a separation column (e.g. distillation column with 10-200 trays), to an energy recovery device such as a turbo-expander to drive an electric generator. Alternatively or in addition, the oxidizer off gas stream can be fed to a steam generator before or after the separation column to generate steam, and if desired, may then be fed to a turbo-expander and pre-heated prior to entry in the expander if necessary to ensure that the off gas does not condense in the turbo-expander.

The oxidation can be conducted in a continuous stirred tank reactor or in a bubble column reactor.

The FDCA formed by the oxidation reaction desirably precipitates out of the reaction mixture. The reaction mixture comprises the oxidizable composition, oxidation solvent composition, and catalyst if a homogeneous catalyst is used, otherwise it comprises the oxidizable composition and oxidation solvent composition.

The product of the oxidation reaction is a crude dicarboxylic acid stream ("cFDCA") comprising solids, said solids comprising FDCA; an oxidation solvent composition; and the intermediate product 5-formyl furan-2-carboxylic acid ("FFCA"). The cFDCA may also contain some amount of FDCA dissolved in the oxidation solvent composition and if used, some of the homogeneous catalyst system. The cFDCA is colored as a result of the production of color by-products. The presence of color bodies can be detected by measuring the b* of the cFDCA composition. The cFDCA composition may also contain mono-carboxylic acid FFCA which is not desirable because it acts to terminate chain growth in a polymerization reaction using an FDCA composition as a reactant.

The cFDCA composition comprises:
a) solids in an amount of at least 5 wt. %, or at least 10 wt %, or at least 15 wt. %, or at least 20 wt. %, or at least 25 wt. %, or at least 28 wt. %, or at least 30 wt. %, or at least 32 wt. %, or at least 35 wt. %, or at least 37 wt. %, or at least 40 wt. %, based on the weight of the cFDCA composition. While there is no upper limit, as a practice the amount will not exceed 60 wt. %, or no greater than 55 wt. %, or no greater than 50 wt. %, or no greater than 45 wt. %., or not greater than 43 wt. %, or not greater than 40 wt %, or not greater than 39 wt %, based on the weight of the cFDCA composition;
b) of the solids in the crude dicarboxylic acid stream, it is desirable that at least 70 wt. %, or at least 80 wt. %, or at least 85 wt. %, or at least 90 wt. %, or at least 95 wt. %, or at least 96 wt. %, or at least 97 wt. %, or at least 98 wt.

%, or at least 99 wt. % of the solids in each case is FDCA based on the weight of the solids;

c) at least 0.1 wt. % FFCA, or at least 0.2 wt. % FFCA, or at least 0.3 wt. % FFCA, or at least 0.35 wt. % FFCA, or at least 0.4 wt. % FFCA, and can contain large amounts of FFCA, such as up to 5 wt. %, or up to 4 wt. %, or up to 3 wt %, or up to 2 wt. %, based on the weight of the cFDCA composition.

Optionally, in addition to FFCA, other by-products can also be present in the cFDCA composition such as color bodies. Color bodies can be formed from impurities present in the oxidizable composition, e.g. 5-HMF composition fed into the oxidation zone, or degradation products produced in the course of the oxidation of the 5-HMF composition. Other by-products besides FFCA present in the cFDCA composition can include, for example, compounds such as 2,5-diformylfuran, levulinic acid, succinic acid, acetoxyacetic acid, 5-(ethoxycarbonyl)furan-2-carboxylic acid ("EFCA"), and their oxidation derivatives. 2,5 diformylfuran can be present, if at all, in an amount of 0 wt % to about 0.2 wt %; levulinic acid in an amount ranging from 0 wt % to 1 wt. % or up to 0.5 wt %; succinic acid in an amount ranging from 0 wt % to 1 wt. %, or up to 0.5 wt %; EFCA in an amount of greater than 0, or at least 0.05 wt %, or at least 0.1 wt %, or at least 0.5 wt % and in each case up to about 4 wt %, or up to about 3.5 wt %, or up to 3 wt. %, or up to 2.5 wt %, or up to 2 wt. %; acetoxyacetic acid in an amount ranging from 0 wt % to 0.5 wt %, and a cumulative amount of the by-products (including FFCA) can be present in an amount ranging from greater than 0 wt. %, or at least 0.1 wt. %, or at least 0.5 wt. %, or at least 1 wt. %, or at least 2 wt. %, an up to 30 wt. %, or up to 20 wt. %, or up to 15 wt. %, or up to 10 wt. %, or up to 5 wt. %, or up to 3 wt. %, or up to 2 wt. %, or up to 1 wt. %., in each case based on the weight of cFDCA composition.

Because some of the by-products present in the cFDCA, the cFDCA composition may be color bodies and/or the cFDCA composition may contain FFCA which is a chain terminating compound, it is desirable to subject the cFDCA composition to a process for the production of a low color product FDCA composition. The cFDCA composition may have a high $b^*$. While the $b^*$ value is not limited, the cFDCA composition will typically have a $b^*$ of more than 3, or more than 4, or more than 5, or more than 6, or more than 7, and may have a $b^*$ as high as 50, or up to 40, or up to 30, or up to 20, or up to 19, or up to 18, or up to 17, or up to 16, or up to 15, or up to 10, or up to 8, or up to 6. Even with a $b^*$ up to 5, or up to 4 it is desirable to purify the cFDCA composition to lower the $b^*$ color. Even though the $b^*$ may not be an important consideration for a particular application, some applications require chain propagation and therefore it is desirable to purify the cFDCA composition to reduce the amount of FFCA present.

While the amount of FFCA present in the cFDCA composition is not limited, the process of the invention is effective to reduce the amount of FFCA present in the cFDCA composition, relative to the amount of FFCA in the product FDCA composition, by a factor of at least 2×, or at least 10×, or at least 100×, or at least 200×, or at least 300×, or at least 350×, or at least 400×, or at least 500×, or at least 750×, or at least 900×, or at least 1000×, or at least 1500×, calculated as:

x reduction=ppm FFCA in cFDCA divided by ppm FFCA in product FDCA composition (where FFCA detected in the product FDCA composition at a value below 1 ppm, or undetectable by virtue of its absence or below the detection limit of an analytical instrument, is, for purposes of this calculation, taken as a value of 1 ppm).

The yield of FDCA in the cFDCA composition, on a solids basis, is at least 60%, or at least 65%, or at least 70%, or at least 72%, or at least 74%, or at least 76%, or at least 78%, or at least 80%, or at least 81%, or at least 82%, or at least 83%, or at least 84%, or at least 85%, or at least 86%, or at least 87%, or at least 88%, or at least 89%, or at least 90%., or at least 91%, or at least 92%, or at least 94%, or at least 95%, and up to 99%, or up to 98%, or up to 97%, or up to 96%, or up to 95%, or up to 94%, or up to 93%, or up to 92%, or up to 91%, or up to 90%, or up to 89%. For example, the yield can range from 70% up to 99%, or 74% up to 98%, or 78% up to 98%, or 80% up to 98%, or 84% up to 98%, or 86% up to 98%, or 88% up to 98%, or 90% up to 98%, or 91% up to 98%, or 92% up to 98%, or 94% up to 98%, or 95% up to 99%.

Yield is defined as mass of FDCA obtained divided by the theoretical amount of FDCA that should be produced based on the amount of raw material use. For example, if one mole or 126.11 grams of 5-HMF are oxidized, it would theoretically generate one mole or 156.09 grams of FDCA. If for example, the actual amount of FDCA formed is only 150 grams, the yield for this reaction is calculated to be=(150/156.09) times 100, which equals a yield of 96%. The same calculation applies for oxidation reaction conducted using 5-HMF derivatives or mixed feeds.

In a second step, the composition of the oxidation solvent composition in the cFDCA composition can be changed by combining a hydrogenation solvent composition with the FDCA solids and dissolving at least a portion of the FDCA solids to thereby produce a solvated FDCA (sFDCA) composition comprising dissolved furan 2,5-dicarboxylic acid (FDCA), the hydrogenation solvent composition, and 5-formyl furan-2-carboxylc acid (FFCA). The sFDCA composition may contain some solids or may be a solution. This step is described further.

The oxidation solvent composition is desirably replaced at least in part with a hydrogenation solvent to avoid producing a large amount of undesirable by-products of the oxidation solvent during hydrogenation. For example, hydrogenation can convert the oxidation solvent acetic acid into ethanol, which then results in having to remove ethanol from the hydrogenated FDCA composition. To avoid the production of any significant quantities of additional by-products that necessitate removal, the oxidation solvent composition is changed or partially or fully replaced before hydrogenation is conducted.

To effect the change or partial or full replacement, a hydrogenation solvent composition is combined with, and desirably added to, the cFDCA composition. The hydrogenation solvent composition is different than the oxidation solvent composition. The difference can be attributed to the use of a hydrogenation solvent composition containing ingredients which are not present in the oxidation solvent composition, or may contain at least one of the same ingredients as in the oxidation solvent composition but where the molar ratio of the solvents within the oxidation solvent composition are different than the molar ratio of solvents within the hydrogenation solvent composition. An example of the latter is a oxidation solvent composition that contains a mixture of a small amount of water in acetic acid at a molar ratio of 2:8, while the hydrogenation solvent composition may contain water at a higher molar ratio (e.g. greater than 2:8 which would also include all water 100:0). Both solvent compositions contain water but each at different molar ratios to either exchange or dilute a portion of one of the ingredients in the oxidation solvent composition (e.g. acetic acid solvent), thereby shifting the solvent composition to one which is more desirable under hydrogenation reaction conditions.

After the solvent swap (the term also includes dilution), the overall concentration of the hydrogenation solvent composition relative to the weight of the solvated FDCA composition can be higher or lower than the concentration of the oxidation solvent composition relative to the weight of the cFDCA composition. In one embodiment, the concentration of hydrogenation solvents in the sFDCA composition is higher than the concentration of oxidation solvents in the cFDCA solution.

The solvent swap systems can include a solid/liquid separation system and optionally an evaporation zone prior to feeding the solid/liquid separation system. The evaporator, if used, is operated to remove a substantial portion of the oxidation solvent (e.g., acetic acid and water) from cFDCA composition. The evaporated oxidation solvent is discharged from the evaporator. The evaporation zone operates to flash the cFDCA composition and cool the cFDCA by evaporative cooling. The evaporator can include multiple zones of evaporation. The evaporation zone can be maintained at a temperature in the range of from about 25 to about 170° C., or in the range of from about 75 to about 150° C.

A concentrated slurry is discharged from the evaporator and fed to the solid-liquid separation zone. Alternatively, the cFDCA stream discharged from the oxidation zone can be fed into the solid dissolved separation zone without first passing through an evaporator. If an evaporator is used, the concentration of solids in the concentrated slurry is desirably increased by at least 20%, or at least 30%, or at least 50% over the concentration of solids in the cFDCA discharged from the oxidation zone. Further, if desired, a portion or all of the feed to the evaporator, such as a flash vessel, can be directed into a by-pass stream and fed directly to the solid-liquid separation zone without entering into the evaporator.

The concentrated slurry can be introduced into solid/liquid separator where at least a portion of the liquid mother liquor is removed from the concentrated slurry. The removed mother liquor is discharged from solid/liquid separator and the resulting wet cake containing residues of the oxidation solvent is washed with at least one wash solvent stream that is desirably the same as the hydrogenation solvent (e.g. water) to remove substantially all of the residual oxidation solvent remaining on the wet cake.

The functions of solid liquid separation and washing the cFDCA may be accomplished in a single solid-liquid separation device or multiple solid-liquid separation devices. The solid-liquid separation zone comprises at least one solid-liquid separation device capable of separating solids and liquids. Additionally, the solid liquid separation device can also perform the function of washing the solids with a wash solvent stream which is the same as the hydrogenation solvent, e.g. water.

Equipment suitable for the solid liquid separation zone can typically be comprised of, but not limited to, the following types of devices: centrifuges of all types including but not limited to decanter and disc stack centrifuges, cross flow filters, solid bowl centrifuges, cyclone, rotary drum filter, belt filter, pressure leaf filter, candle filter, a continuous pressure drum filter, or more specifically a continuous rotary pressure drum filter. The solid-liquid separator may be operated in continuous or batch mode, although it will be appreciated that for commercial processes, the continuous mode is preferred. A suitable pressure filter which can be employed as the solid/liquid separator is a BHS-FEST™, available from BHS-WERK, Sonthofen, D-8972, Sonthofen, West Germany.

The temperature of the wash solvent can range from 20° C. to 180° C., or 40° C. and 150° C., or 50° C. to 130° C. The amount of wash solvent used is defined as the wash ratio and equals the mass of wash divided by the mass of solids on a batch or continuous basis. The wash ratio can range from about 0.3 to about 5, about 0.4 to about 4, and preferably from about 0.5 to 3.

The wash feed is desirably formed primarily of water. Most preferably the wash feed consists essentially of water. There may exist more than one wash zone.

The washed cFDCA cake is discharged from the solid liquid separation zone and fed to a dissolution zone for dissolving the washed cFDCA cake into a hydrogenation solvent composition useful in hydrogenation reactions. The source of the hydrogenation solvent composition can come from the wash solvent or from the dissolution solvent stream provided into the dissolution zone or both.

The hydrogenation solvent composition desirably comprises a solvent which dissolves at least a portion of the FDCA solids under conditions used in the hydrogenation reaction zone and which does not itself convert to other products which must be separated in any appreciable amount, e.g more than 20% conversion of the types of products requiring removal. Suitable hydrogenation solvent compositions include water and steam. Desirably, the hydrogenation solvent composition comprises at least 80 wt. % water, or at least 90 wt. % water, or at least 95 wt. % water, or at least 99 wt. % water, or at least 100 wt. % water.

In the dissolution zone, it may be necessary to elevate the temperature of the cFDCA solids when combined with the hydrogenation solvent composition to dissolve at least a portion of the FDCA solids into the hydrogenation solvent composition. The hydrogenation solvent and washed cFDCA solids are desirably combined at a solvent-to-solids weight ratio in the range of from about 0.5:1 to about 50:1, or in the range of from 1:1 to 20:1, or in the range of from 1:1 to 15:1, or in the range of from 1:1 to 10:1, or in the range of from 1.5:1 to 5:1.

Suitable dissolution temperatures are those effective to dissolve the desired amount of FDCA solids into solution. The hydrogenation solvent composition may be added at (by pre-heating) or heated in the dissolution zone to a temperature of at least 120° C. under a pressure and time sufficient to allow for at least 80 wt. % dissolution, although to reduce the time required for dissolution, it is desirable that the hydrogenation solvent composition temperature is at least 130° C., or at least 135° C., or at least 140° C., or at least 150° C. The hydrogenation solvent temperature does not need to exceed 240° C., or 220° C., or 200° C., or even 190° C., or even 180° C. As seen in FIG. 1, the solubility of FDCA in water at ambient pressure increases dramatically as the temperature of the water increases beyond 130° C.

It is desired to dissolve at least 80 wt. %, or at least 90 wt. %, or at least 95 wt. %, or at least 98 wt. %, or at least 99 wt. % or at least 99.5 wt. % of the solids in the cFDCA solution to produce a solvated FDCA composition ("sFDCA"). The sFDCA composition comprises dissolved furan 2,5-dicarboxylic acid (FDCA), hydrogenation solvent composition in an amount of at least 30 wt. % based on the weight of the sFDCA composition, and 5-formyl furan-2-carboxylc acid (FFCA).

An example of the sFDCA composition comprises:
a) less than 5 wt. %, or less than 4 wt. %, or less than 3 wt. %, or less than 2 wt. %, or less than 1 wt. %, or less than 0.5 wt. %, or less than 0.1 wt. %, or less than 0.01 wt. % solids;
b) dissolved FDCA in an amount of greater than 0, or at least 1 wt. %, or at least 2 wt. %, or at least 5 wt. %, or at least 7 wt. %, or at least 9 wt. %, or at least 10 wt. %, or at least 12 wt. %, or at least 15 wt. %, based on the weight of the sFDCA composition. The upper limit is not particularly limited, but amount of up to 50 wt. %, or up to 45 wt. %, or up to 40 wt. %, or up to 35 wt. %, or up to 30 wt. %, or up to 25 wt. %, or up to 20 wt. %, or up to 15 wt. %, or up to 12 wt. %, based on the weight of the sFDCA composition, are useful; and c) a hydrogenation solvent in an amount of at least 30 wt. %, or at least 35 wt. %, or at least 40 wt. %, or at least 45 wt. %, or at least 50 wt. %, or at least 55 wt. %, or at least 55 wt. %, or at least 60 wt. %, or at least 65 wt. %, or at least 70 wt. %, or at least 75 wt. %, or at least 80 wt. %, and up to 98 wt. %, or up to 95 wt. %, or up to 92 wt. %, or up to 90 wt. %, or up to 85 wt. %, or up to 80 wt. %, or up to 75 wt. %, or up to 70 wt. %, or up to 65 wt. %, or up to 60 wt. %, or up to 55 wt. %, or up to 50 wt. %, based on the weight of the sFDCA composition; and d) FFCA in an amount of at least greater than 0, or at least 0.005 wt. % FFCA, or at least 0.01 wt. % FFCA, or at least 0.05 wt. % FFCA, or at least 0.1 wt. % FFCA, or at least 0.25 wt. % FFCA, based on the weight of the sFDCA composition. There is not particular upper limit and the amount can contain 3 wt. % or less, or up to 2.5 wt. %, or up to 2 wt %, or up to 1.5 wt. %, based on the weight of the sFDCA composition.

One advantage of the invention is that FDCA solubilizes in water at much lower temperatures than the temperatures required to dissolve terephthalic acid in water, thereby reducing the energy requirements for obtaining a solution adequate for hydrogenation. Although good solubility is also obtained at very high hydrogenation solvent temperatures, it is not necessary to employ such high temperatures to obtain a solution. Thus, the hydrogenation solvent temperature does not need to exceed 240° C., or 225° C., or 200° C., or even 190° C., or even 180° C. to obtain a solvated FDCA solution. The solvated FDCA solution fed into the hydrogenation reaction zone within the hydrogenation reactor can be at a temperature within the range of 130°-200°, or 135° C.-200° C., or 140° C.-200° C., or 145° C.-200° C., or 150° C.-200° C., or 130° C.-190° C., or 135° C.-190° C., or 140° C.-190° C., or 145° C.-190° C., or 150° C.-190° C., or 130° C.-185° C., or 135° C.-185° C., or 140° C.-185° C., or 145° C.-185° C., or 150° C.-185° C., or 130° C.-180° C., or 135° C.-180° C., or 140° C.-180° C., or 145° C.-180° C., or 150° C.-180° C., or 130° C.-175° C., or 135° C.-175° C., or 140° C.-175° C., or 145° C.-175° C., or 150° C.-175° C.

After providing a sFDCA solution, it is subjected to a hydrogenation reaction in a hydrogenation reaction zone under conditions sufficient to cause hydrogenation of at least a portion of FFCA, and desirably color bodies. In particular, the sFDCA composition is exposed to hydrogenation conditions in a hydrogenation zone at a temperature within a range of 130° C. to 225° C. by contacting the sFDCA composition with hydrogen in the presence of a hydrogenation catalyst under a hydrogen partial pressure within a range of 10 psi to 900 psi, to thereby produce a hydrogenated furan 2,5-dicarboxylic acid composition (hFDCA) comprising dissolved FDCA, hydrogenated FFCA, and said hydrogenation solvent. In the process of the invention, the cFDCA is purified by catalytic hydrogenation of the by-products in the following non-limiting types of reactions:

(5)

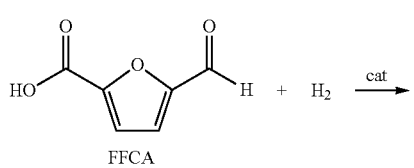

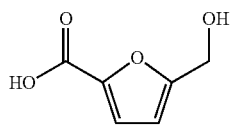

5-(hydroxymethyl)furan-2-carboxylic acid (5-HMFCA)

(6)

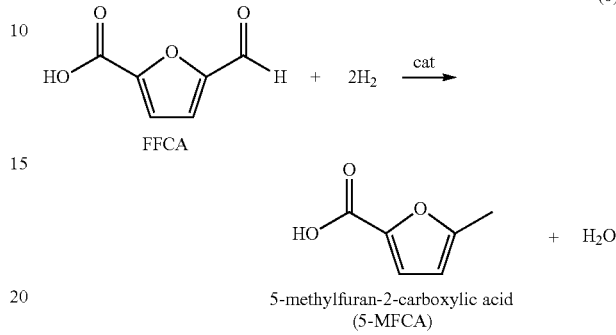

5-methylfuran-2-carboxylic acid (5-MFCA)

(7)

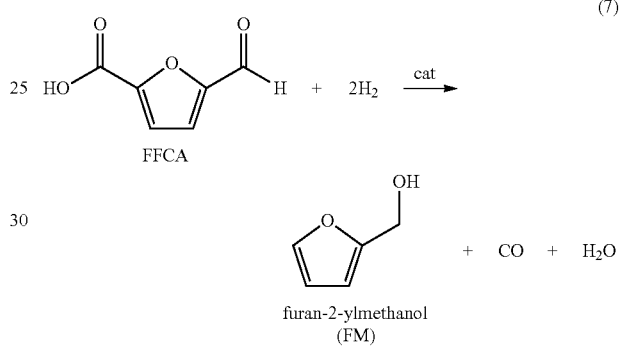

furan-2-ylmethanol (FM)

(8)

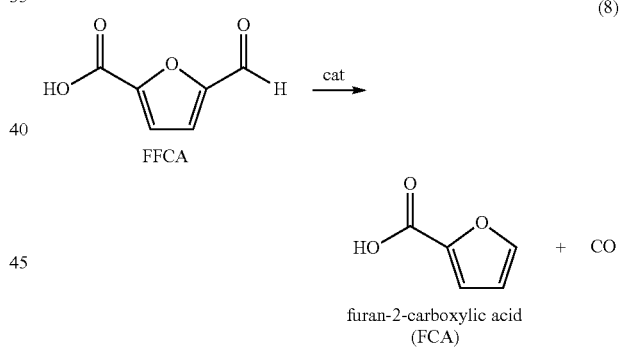

furan-2-carboxylic acid (FCA)

As can be seen in the reaction equations above, the intermediate FFCA is converted to 5-HMFCA, 5-MFCA, FCA and FM, all of which are water soluble and can be separated easily from FDCA through any number of techniques, such as crystallization. In addition, unsaturation in the colored bodies is converted to saturated species to thereby remove color, and they can either be removed from the product FDCA or can remain in or on the FDCA product.

The sFDCA solution is introduced into a hydrogenation vessel where the solution is contacted, in the hydrogenation reaction zone, with hydrogen and a hydrogenation catalyst. In the process of the invention, hydrogenation is carried out under mild conditions while effectively and dramatically reducing the amount of FFCA and color bodies. By carrying out hydrogenation under mild conditions, selective hydrogenation can be conducted to minimize hydrogenating the furan ring of the FDCA molecule while selectively hydrogenating FFCA and color bodies, compared to conducting hydrogenation under higher temperature and pressure. Further, less energy is consumed to obtain a desired level of intermediate species which result in chain termination and to obtain the desired level of color in the final product. A further advantage of carrying out hydrogenation under mild conditions is the diminished risk of degrading the FDCA molecule.

Hydrogenating the sFDCA solution at a temperature within a range of 130° C. to 225° C., or even less than 200° C., is effective to obtain the desired level of FFCA and color reduction. The mild hydrogenation temperature in the hydrogenation reaction zone can be at a temperature within a range of 130° C.-225° C., or 130° C.-205° C., or 130° C.-200° C., or 130° C. to less than 200° C., or 135° C. to less than 200° C., or 140° C. to less than 200° C., or 145° C. to less than 200° C., or 150° C. to less than 200° C., or 130°-195°, or 135°-195°, or 140°-195°, or 145°-195°, or 150°-195°, or 130° C.-190° C., or 135° C.-190° C., or 140° C.-190° C., or 145° C.-190° C., or 150° C.-190° C., or 130° C.-185° C., or 135° C.-185° C., or 140° C.-185° C., or 145° C.-185° C., or 150° C.-185° C., or 130° C.-180° C., or 135° C.-180° C., or 140° C.-180° C., or 145° C.-180° C., or 150° C.-180° C., or 130° C.-175° C., or 135° C.-175° C., or 140° C.-175° C., or 145° C.-175° C., or 150° C.-175° C. The hydrogenation temperature is determined by the temperature of the liquid at or near the liquid discharge port of the hydrogenation reactor in a continuous process or by a thermocouple within the liquid inside the hydrogenation reactor in a batch process.

The partial pressure of hydrogen in the hydrogenation reaction zone within the hydrogenation reactor is also reduced to thereby consume less hydrogen while maintaining a good reduction of FFCA and color in the resulting product FDCA. The partial pressure of hydrogen in the hydrogenation zone is desirably sufficient to drive at least a portion of the hydrogen into solution. In addition, the partial pressure selected is dependent upon the reaction temperature selected. To avoid hydrogenating the furan ring, the partial pressure of hydrogen should be controlled at a given reaction temperature. A lower hydrogen partial pressure should be selected if the reaction temperature is at a high, while higher hydrogen partial pressures can be selected if the reaction temperature is low. The particular values selected within each of the pressure and temperature ranges disclosed above should be effective to lower the b* color and presence of FFCA while minimizing formation of THFDCA (the hydrogenated FDCA ring). The partial pressure of hydrogen can vary from 10 psig to 900 psi, or from 20 psi to 900 psi, or from 50 psi to 900 psi, or from 20 psi to 750 psi, or from 50 psi to 750 psi, or from 20 psi to 600 psi, or from 50 psi to 600 psi, or from 20 psi to 500 psi, or from 50 psi to 500 psi, or from 20 psi to 400 psi, or from 50 psi to 400 psi, or from 20 psi to 300 psi, or from 50 psi to 300 psi, or from 20 psi to 250 psi, or from 50 psi to 250 psi, or from 20 psi to 200 psi, or from 50 psi to 200 psi, or from 20 psi to 150 psi, or from 50 psi to 150 psi, or from 20 psi to 100 psi, or from 50 psi to 100 psi, or from 20 psi to 90 psi, or from 50 psi to 90 psi. The hydrogen partial pressure is calculated by subtracting the vapor pressure of water or combination of hydrogenation solvents at the reaction temperature from the total reactor pressure.

The total pressure within the hydrogenation reaction zone is also desirably effective to provide a reduction of FFCA and color in the resulting product FDCA without formation of high amounts of THFDCA while also sufficient to drive the hydrogen into solution. The total pressure can vary from 35 psig to less than 950 psig, or from 50 psig to less than 950 psig, or from 70 psig to less than 950 psig, or from 35 psig to 930 psig, or from 50 psig to 930 psig, or from 70 psig to 930 psig, or from 35 psig to 900 psig, or from 50 psig to 900 psig, or from 70 psig to 900 psig, or from 35 psig to 800 psig, or from 50 psig to 800 psig, or from 70 psig to 800 psig, or from 35 psig to 650 psig, or from 50 psig to 650 psig, or from 70 psig to 650 psig, or from 35 psig to 550 psig, or from 50 psig to 550 psig, or from 70 psig to 550 psig, or from 35 psig to 350 psig, or from 50 psig to 350 psig, or from 70 psig to 350 psig, or from 35 psig to 300 psig, or from 50 psig to 300 psig, or from 70 psig to 300 psig, or from 35 psig to 250 psig, or from 50 psig to 250 psig, or from 70 psig to 250 psig, or from 35 psig to 200 psig, or from 50 psig to 200 psig, or from 70 psig to 200 psig, or from 35 psig to 150 psig, or from 50 psig to 150 psig, or from 70 psig to 150 psig, or from 35 psig to 130 psig, or from 50 psig to 130 psig, or from 70 psig to 130 psig.

The molar ratio of hydrogen fed to the hydrogenation reaction zone to moles of FDCA fed to the hydrogenation zone is desirably in the range of from 0.01:1 to 2:1, or 0.02:1 to 1:1, or from 0.02:1 to less than 1:1, or from 0.02:1 to 0.8:1, or from 0.02:1 to 0.5:1, or from 0.02:1 to 0.1:1, or from 0.02:1 to 0.08:1, or from 0.02:1 to 0.06:1.

Hydrogen can be fed into the hydrogenation reaction zone pure at a 100 mole % hydrogen concentration or as a mixed feed with other inert gases. The concentration of hydrogen fed into the reaction zone is not particularly limited. Suitable amounts can be at least 80 wt. %, or at least 90 wt. %, or at least 95 wt. %, or at least 98 wt. %, or at least 99.5 wt. %.

The residence time is effective to reduce the b* color of the sFDCA composition and reduce the amount of FFCA while minimizing the formation of THFDCA at the reaction temperature and catalyst type and loading selected. Examples of suitable residence times of the sFDCA in the hydrogenation reaction zone can range from 15 minutes to 10 hours, and 45 minutes to about 5 hours are useful and commercially practical.

The process of the present invention can be operated in a variety of configurations. One such configuration is a fixed bed flow reaction system. Desirably, the hydrogenation reaction is conducted in a fixed bed flow reaction system. The substrate to be hydrogenated, the sFDCA solution, is in the liquid phase in the hydrogenation reaction zone. Another type of suitable configuration is a trickle bed configuration. Regardless of the method of operation, the desired time of contact between the sFDCA solution, hydrogen, and catalyst components can be varied as desired to achieve the desired level of reaction.

The sFDCA solution is contacted with a hydrogenation catalyst in the hydrogenation reaction zone. Any conventional hydrogenation catalyst may be employed. The hydrogenation catalyst employed in the hydrogenation zone/vessel can be a noble Group VIII metal on a conventional catalyst carrier or support material such as carbon. Although palladium on carbon is a typical hydrogenation catalyst, it is possible to use catalysts containing other platinum group metals such as ruthenium, rhodium, osmium, iridium and platinum, or an oxide of such a metal or by a metallic catalyst like Pd and/or Rh on carbon. It is also possible to use layered catalyst beds consisting of a layer of Rh on carbon catalyst before or after the bulk of Pd on carbon catalysts.

The carbon support material can be granular, in pellet form, or any other particle form. The size of the particles is not limited. The type of carbon used is also not limited. Activated carbon can be used, and a support having a surface area of at least 200 m2/gm (measured by the BET Method) without any upper limit can also be used. A support having a surface area within a range of 200 to 3000 m2/gm is suitable.

The loading of metal onto the support can be from 0.01 wt. % up to 5 wt. %, or from 0.01 to 1.0 wt. %, based on the weight of the final catalyst composition (including the support). The amount of catalyst metal loaded into the reaction zone is effective to obtain the desired degree of conversion without excessive production of THFDCA. The moles of FFCA fed into the hydrogenation reactor per hour to the moles of total catalyst metal(s) employed can be at least $0.1\ hr^{-1}:1$, or at least $1\ hr^{-1}:1$, or at least $5\ hr^{-1}:1$, or at least $10\ hr^{-1}:1$, and can be as high as desired. Consideration should be given to the lower limit of the stated ratio to avoid using an excessive amount of total catalyst metal(s) relative to the moles of FFCA fed that could lead to the formation of excessive amounts of THFDCA. An excessive amount of catalyst metal can lead to hydrogenation of not only FFCA but also higher amounts of FDCA to convert FDCA to THFDCA, leading to a yield loss of product. Suitable molar ratios of FFCA fed per hour to moles of catalyst metal can be up to $150\ hr^{-1}:1$, or up to $125\ hr^{-1}:1$, or up to $100\ hr^{-1}:1$.

The hydrogenation reactor can be any conventional hydrogenation vessel. One example is a hollow cylindrical vessel that horizontally or vertically oriented, desirably is vertically oriented, in which the sFDCA solution is introduced into the hydrogenation reactor at or near the top of the vertical vessel or at one end of a horizontal vessel, and in the presence of hydrogen flows down through the reaction chamber or zone and over a fixed catalyst bed supported by mesh, wire, or perforated plates in a vertical vessel or across the catalyst bed in a horizontally oriented reactor. The hydrogenated FDCA solution is discharged from the hydrogenation reactor at or near the bottom of the reactor in a vertical reactor or at an end that is distal from the entry point in a horizontally oriented reactor. The reactor can be liquid full or may have a gas head above the liquid level of the sFDCA solution, but the liquid level should at least submerge the catalyst beds. If not liquid full, the reactor can be operated to maintain a constant liquid level by feeding hydrogen gas into the gas space at a rate sufficient to maintain a constant liquid level. If operated liquid full, the hydrogen can be dissolved in at least a portion of the sFDCA solution with a flow meter and fed into the hydrogenation reaction zone as a dissolved hydrogen FDCA solution.

During the hydrogenation process, the following undesired reactions in equations 9, 10, or 11 may occur if the hydrogenation conditions are too severe, either because the hydrogenation temperature is too high for the residence time (or average hourly space velocity) employed, or the partial pressure of hydrogen is too high, or the catalyst loading is too high, or a combination of two or more of these activities:

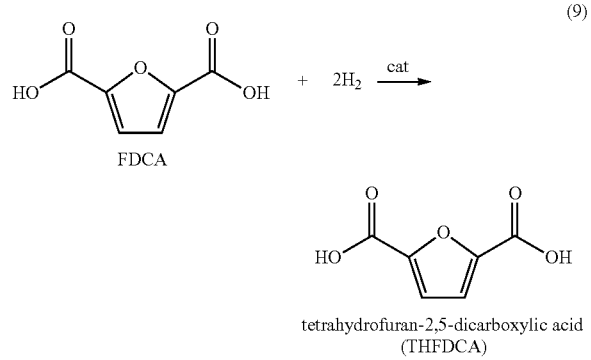

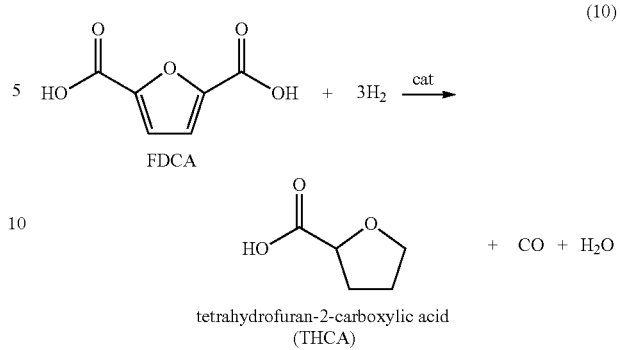

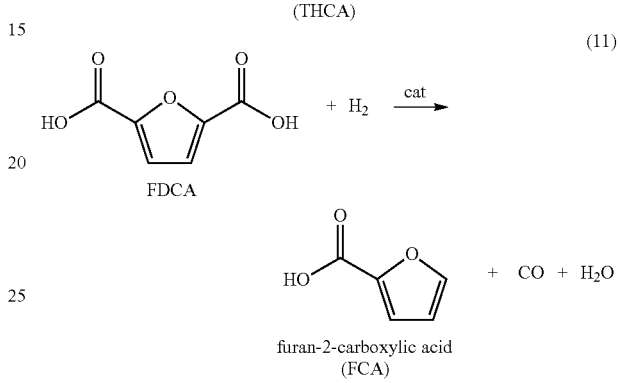

Hydrogenating under conditions that are too severe results in hydrogenating the furan ring, or dissociating a carboxylic acid group from the furan ring, or a combination of both. Thus, it is desirable to conduct the hydrogenation reaction under conditions effective such that the hydrogenated FDCA composition (hFDCA) contains no more than 2 wt. % of THFDCA, or no more than 1.5 wt. %, or no more than 1 wt. %, or no more than 0.8 wt. %, or no more than 0.7 wt. %, or no more than 0.6 wt. %, or no more than 0.5 wt. %, or no more than 0.4 wt. %, or no more than 0.3 wt. %, or no more than 0.1 wt. % THFDCA, based on the weight of the hFDCA composition, which includes liquid and solids. While higher amounts of THFDA can be contained within the hFDCA composition, such as less than 10 wt. % THFDCA, or no more than 5 wt. % THFDCA and greater than 2 wt. %, based on the weight of the hFDCA composition, such high amount of THFDCA represent a high loss of yield, and a commercial process would become impractical to maintain.

Following hydrogenation, the hydrogenated FDCA solution can be recovered and purified using conventional techniques well known to those of skill in the art. At least a portion of the dissolved FDCA in the hFDCA is converted to a solid FDCA to thereby produce a product FDCA (pFDCA) composition. For example, at least a portion of the intermediates and color bodies which were hydrogenated can be separated from FDCA in the hFDCA solution by any conventional techniques, such as crystallization to form a crystallized FDCA composition in which at least some of the hydrogenated intermediates (FFCA) and color bodies stay soluble in hydrogenation solvent (e.g. water) and FDCA crystallizes to form FDCA solids. The FDCA solids can be separated from the crystallized FDCA solution by solid liquid separation in which the liquids containing at least a portion of the hydrogenated byproducts (FFCA) and some color bodies are separated as a mother liquor, optionally followed by washing to wash away any residual mother liquor as a wash waste stream, which can be combined with the mother liquor stream if desired.

Instead of or in addition to crystallization, other separation techniques can be employed for isolating FDCA, such as distillation, solvent/solvent extraction, and the like.

If desired, before crystallization, any carbon particulates separated from the carbon bed and entrained into the hFDCA composition can be separated from the hFDCA solution by filtration (e.g. pressure filtration, depth filtration), decantation, and the like.

Desirably, after the optional filtration step to remove carbon bed particulates from the hydrogenation reactor, the hydrogenated FDCA solution is crystallized in at least one crystallizer. In the crystallizer, the temperature of the hydrogenated solution is lowered to a temperature effective to precipitate at least a portion of the FDCA in the hydrogenated FDCA solution. The crystallization temperature can be in the range of from about 50 to about 200° C., or from about 75 to about 140° C., or from 50 to 120° C. Desirably, the crystallization temperature is at least 20° C. lower, or at least 30° C. lower, or at least 40° C. lower than the temperature of the hydrogenated FDCA solution feeding the crystallizer. The crystallization temperature is desirably above the temperature at which the hydrogenated intermediates and color bodies would precipitate. If the temperature drop is too sudden and severe, an excessive amount of the hydrogenated intermediates and color bodies can become encapsulated within the FDCA crystals and the size of the crystals remain fine. Thus, one may employ multiple crystallizers in stages that step down the temperature to the desired end point to increase crystal size and minimize encapsulating by-products instead of dropping the temperature to the desired end point in one step.

The decreased temperature in crystallization system causes the majority (more than 50 wt. %, or at least 75 wt. %, or at least 80 wt. %, or at least 90 wt. %, or at least 95 wt. %, or at least 98 wt. %, or at least 99 wt. %) of the FDCA dissolved in the hydrogenated FDCA solution to crystallize, thereby forming solid particles of a FDCA in a crystallized FDCA composition. The crystallized FDCA composition contains FDCA solid particles and in the liquid phase the hydrogenated intermediates and color bodies such as 5-HMFCA, 5-MFCA, FCA, FM and other hydrogenated impurities remain in solution.

The two-phase crystallized FDCA composition (slurry) discharged from the crystallizer(s) can thereafter be subjected to solid/liquid separation in a conventional separator, optionally followed by washing with a wash solvent. The separated FDCA solids can be dried in one or more conventional dryers to produce a product FDCA composition that is purified. Alternatively, a pFDCA composition can be in the form of a wet cake by avoiding the drying step.

The pFDCA composition desirably has the following composition:
a) solids, wherein at least 95 wt. %, or at least 97 wt. %, or at least 98 wt. %, or at least 99 wt. %, or at least 99.5 wt. %, or at least 99.8 wt. %, or at least 99.9 wt. %, or at least 99.95 wt. % of the solids are FDCA, based on the weight of the solids;
b) a b* of at least zero and less than 4, or less than 3, or less than 2, or less than 1.5, or less than 1, or less than 0.8, or less than 0.5;
c) FFCA in an amount of less than 500 ppm, or less than 200 ppm, or less than 100 ppm, or less than 50 ppm, or less than 25 ppm, or less than 20 ppm, or less than 15 ppm, or no more than 10 ppm;
d) and THFDCA present in an amount ranging from zero, or greater than zero, or at least 1 ppm, or at least 2 ppm, or at least 5 ppm, or at least 10 ppm, or at least 20 ppm, or at least 30 ppm, or at least 50 ppm, and in an amount of no more than 0.5 wt. %, or less than 0.4 wt. %, or less than 0.3 wt. %, or less than 0.1 wt. % THFDCA, or less than 500 ppm, or not more than 100 ppm, or not more than 50 ppm, or not more than 30 ppm, or not more than 25 ppm, or not more than 20 ppm, or not more than 15 ppm, in each case based on the weight of the solids.

In one embodiment, the pFDCA composition desirably comprises at least 98 wt. % solids, or at least 99 wt. % solids, or at least 99.5 wt. % solids, or at least 99.9 wt. % solids, or at least 99.5 wt. % solids. This embodiment would represent an isolated dried solids product.

In another embodiment, the product FDCA composition desirably contains at least 2 wt. % liquid, or at least 4 wt. % liquid, or at least 6 wt. % liquid, and up to 40 wt. % liquid, or up to 30 wt. % liquid, or up to 20 wt. % liquid, or up to 15 wt. % liquid, with the remainder solids, and the solid comprise at least 99 wt. % FDCA and FFC and THFDCA in any of the amounts mentioned above. This embodiment would represent a wet cake product.

A very low b* can be obtained in the product FDCA composition by hydrogenating the cFDCA composition. The b* is one of the three-color attributes measured on a spectroscopic reflectance-based instrument. The color can be measured by any device known in the art. A Hunter Ultrascan XE instrument is typically the measuring device. Positive readings signify the degree of yellow (or absorbance of blue), while negative readings signify the degree of blue (or absorbance of yellow). The described and claimed b* values are on the FDCA solids, or a composition containing FDCA solids, that are dissolved into a solution, regardless of how the sample is initially prepared (e.g. whether or not the samples are prepared for removal of carbon residuals). All of the b* values reported, described or claimed with respect to FDCA (whether a cFDCA, hFDCA, or pFDCA) are based on the solution method of measuring the b* of the FDCA solids, and this technique is described with more particularity in the examples.

The process can be operated on a commercial scale. Examples of suitable rates for the production of a pFDCA composition include an average of at least 1,000 kg/day, or at least 10,000 kg/day, or at least 20,000 kg/day, or at least 50,000 kg/day, or at least 75,000 kg/day, or at least 100,000 kg/day, or at least 200,000 kg/day of a pFDCA composition on a solids basis, on a 24 hour basis over the course of any three months.

The pFDCA composition, which can be either dried carboxylic acid solids or wet cake, comprising FDCA can be fed to the esterification reaction zone. The pFDCA composition can be shipped via truck, ship, or rail as solids.

The process for making the pFDCA composition can be integrated with the process for the manufacture of an esterification facility to make a diester or a polyester. An integrated process includes co-locating the two manufacturing facilities, one for hydrogenation, and the other for esterification, within 10 miles, or within 5 miles, or within 2 miles, or within 1 mile, or within ½ mile of each other. An integrated process also includes having the two manufacturing facilities in solid or fluid communication with each other. If a solid dicarboxylic acid composition is produced, the solids can be conveyed by any suitable means, such as air or belt, to the esterification facility. If a wet cake dicarboxylic acid composition is produced, the wet cake can be moved by belt or pumped as a liquid slurry to the facility for esterification.

The invention has been described in detail with particular reference to preferred embodiments thereof, but will be understood that variations and modification can be affected within the spirit and scope of the invention.

Examples 1-12

In Examples 1-12 a 300 mL titanium autoclave equipped with a catalyst basket was charged with 45.0 g of crude colored FDCA (starting b* shown in Table 1) that contained some FFCA and 450.0 g of water. The catalyst basket was charged with 3 grams of a palladium/carbon catalyst containing 0.5 wt % palladium in an amount as shown in Table 1. The autoclave was sealed and heated to the desired temperature while agitating the mixture. $H_2$ gas was introduced to attain the various hydrogen partial pressures listed in Table 1. The total pressure was maintained from a surge tank during the reaction. The reaction continued for the period of time stated in Table 1, upon which the gas supply was stopped and the autoclave was cooled to room temperature to thereby crystallize FDCA and then depressurized. The heterogeneous mixture was filtered to isolate the pFDCA. The mass of the mother liquor filtrate was recorded. The pFDCA solid was washed with 100 mL of water three times and it was oven dried at 110° C. under vacuum overnight and then weighed. The washed and dried solid was analyzed by Gas Chromatography using BSTFA derivatization method, HPLC method and solution CIE color measurement method. The mother liquor filtrate, before washing and drying, was also analyzed but only by Gas Chromatography using BSTFA derivatization method to detect the amount of THFDCA. The analytical techniques used are further described below. Table 1 sets forth the results of mild hydrogenation of crude FDCA along with results from Example 10 which subjected the crude FDCA to hydrogenation conditions conducive to the formation of high amounts of THFDCA.

The specific methodology one may employ to detect the amount of THFDCA, FFCA, FDCA, and b* are now described.

Gas Chromatographic Method for FDCA Solid Analysis:

Process samples were analyzed using a Shimadzu gas chromatograph Model 2010 (or equivalent) equipped with a split/heated injector (300° C.) and a flame ionization detector (300° C.). A capillary column (60 meter×0.32 mm ID) coated with (6% cyanopropylphenyl)-methylpolysiloxane at 1.0 μm film thickness (such as DB-1301 or equivalent) was employed. Helium was used as the carrier gas with an initial column head pressure of 29.5 psi and an initial column flow of 3.93 mL/minute while the carrier gas linear velocity of 45 cm/second was maintained constant throughout the entire oven temperature program. The column temperature was programmed as follows: The initial oven temperature was set at 80° C. and was held for 6 minutes, the oven was ramped up to 150° C. at 4° C./minute and was held at 150° C. for 0 minute, the oven was ramped up to 240° C. at 10° C./minute and was held at 240° C. for 5 minutes, then the oven was ramped up to 290° C. at 10° C./minute and was held at 290° C. for 17.5 minutes (the total run time was 60 mins). 1.0-μl of the prepared sample solution was injected with a split ratio of 40:1. EZ-Chrom Elite chromatography data system software was used for data acquisition and data processing. The sample preparation was done by weighing 0.1 g (accurate to 0.1 mg) of sample in a GC vial and adding 200.0 μl ISTD solution (1% by volume of decane in pyridine) and 1000 μl of BSTFA (N,O-bis(trimethylsilyl)trifluoroacetamide) with 1% TMSCl (trimethylchlorosilane) to the GC vial. The content was heated at 80° C. for 30 minutes to ensure complete derivitization. 1.0-μl of this prepared sample solution was injected for GC analysis.

Gas Chromatographic Method for Detecting THFDCA (wt % Method):

Process samples were analyzed using a Shimadzu gas chromatograph Model 2010 (or equivalent) equipped with a split/splitless, heated injector (300° C.) and a flame ionization detector (300° C.). A capillary column (60 meter×0.32 mm ID) coated with a proprietary stationary phase (ZB-Multi-Residue-1) at 0.5 μm film thickness was employed. Helium was used as the carrier gas with an initial column head pressure of 11.5 psi and an initial column flow of 1.24 mL/minute while the carrier gas linear velocity of 19.7 cm/second was maintained constant throughout the entire oven temperature program. The column temperature was programmed as follows: The initial oven temperature was set at 50° C. and was held for 20 minutes, the oven was ramped up to 280° C. at 10° C./minute and was held at 280° C. for 17 minute (the total run time was 60 mins). 1.0-μl of the prepared sample solution was injected with a split ratio of 60:1. EZ-Chrom Elite chromatography data system software was used for data acquisition and data processing. The sample preparation was done by weighing 0.0280-0.0300 g (accurate to 0.1 mg) of sample in a GC vial and adding 200.0 μl ISTD solution (1% by volume of decane in pyridine) and 1000 μl of BSTFA (N,O-bis(trimethylsilyl)trifluoroacetamide) with 1% TMSCl (trimethylchlorosilane) to the GC vial. The content was heated at 80° C. for 45 minutes to ensure complete derivitization. 1.0-μl of this prepared sample solution was injected for GC analysis.

Gas Chromatographic Method for Detecting THFDCA (ppm Method):

Process samples were analyzed using a Shimadzu gas chromatograph Model 2010 (or equivalent) equipped with a split/splitless, heated injector (300° C.) and a flame ionization detector (300° C.). A capillary column (60 meter×0.32 mm ID) coated with a proprietary stationary phase (ZB-Multi-Residue-1) at 0.5 μm film thickness was employed. Helium was used as the carrier gas with an initial column head pressure of 11.5 psi and an initial column flow of 1.24 mL/minute while the carrier gas linear velocity of 19.7 cm/second was maintained constant throughout the entire oven temperature program. The column temperature was programmed as follows: The initial oven temperature was set at 50° C. and was held for 5 minutes, the oven was ramped up to 280° C. at 10° C./minute and was held at 280° C. for 32 minute (the total run time was 60 mins). 1.0-μl of the prepared sample solution was injected splitless. EZ-Chrom Elite chromatography data system software was used for data acquisition and data processing. The sample preparation was done by weighing 0.0280-0.0300 g (accurate to 0.1 mg) of sample in a GC vial and adding 200.0 μl ISTD solution (1% by volume of decane in pyridine) and 1000 μl of BSTFA (N,O-bis(trimethylsilyl) trifluoroacetamide) with 1% TMSCl (trimethylchlorosilane) to the GC vial. The content was heated at 80° C. for 45 minutes to ensure complete derivitization. 1.0-μl of this prepared sample solution was injected for GC analysis.

Liquid Chromatographic Method for Low Levels of FFCA in FDCA:

Samples were analyzed with an Agilent 1200 LC unit consisting of a quaternary pump, an autosampler (3 uL injection), a thermostated column compartment (35 C) and a diode array UV/vis detector (280 nm). The chromatograph was fitted with a 150 mm×4.6 mm Thermo Aquasil C18 column packed with 5 micron particles. The solvent flow program is shown in the table below: Channel A was 0.1% phosphoric acid in water, channel B was acetonitrile, and channel C was tetrahydrofuran (THF)

| Time (min) | % A | % B | % C | Flow (ml/min) |
|---|---|---|---|---|
| Initial | 95.0 | 0.0 | 5.0 | 1.50 |
| 7 | 95.0 | 0.0 | 5.0 | 1.50 |
| 10 | 15.0 | 80.0 | 5.0 | 1.50 |
| 12 | 15.0 | 80.0 | 5.0 | 1.50 |
| 12.1 | 95.0 | 0.0 | 5.0 | 1.50 |
| 15 | 95.0 | 0.0 | 5.0 | 1.50 |

Equilibration time: 1 minute

EZChrom elite is used for control of the HPLC and for data processing. A 5 point linear calibration was used in the (approximate) range of 0.25 to 100 ppm FFCA. Samples were prepared by dissolving ~0.05 g (weighed accurately to 0.0001 g) in 10 ml of 50:50 DMF/THF; higher sample weights may be used for samples where the FFCA is present at a very low level, provided that the solubility of FDCA is not exceeded. Sonication was used to ensure complete dissolution of the sample in the solvent. A portion of the prepared sample was transferred to an auto sampler vial for injection onto the LC.

Sample Preparation for b* Measurement

Since hydrogenated FDCA was made in an autoclave without fixing the Pd/C catalyst in a bed, and some the carbon particulates became encapsulated within the FDCA solids, to obtain the true b* of the FDCA composition, some of the carbon particulates were first separated. A 10 wt % NH$_4$OH stock solution was prepared by diluting commercial 30 wt % NH$_4$OH with water. 5.0 g of a dry FDCA solid was dissolved in 45.0 g of 10 wt % NH$_4$OH solution. The mixture was filtered using GHP Acrodisc 25 mm Syringe Filter to remove catalyst carbon particles. The b* of the solution was measured as discussed below:

Method for Measurement of b*

Samples were analyzed using a Hunter Lab UltraScan Pro spectrophotometer with an integrating light sphere. Per manufacturer recommendation the spectrophotometer was set to the CIELAB color scale with the D65 illuminate and 10° observer. The samples (in this case a 10 wt % NH$_4$OH stock solution) were transferred to a clear, disposable transmission cells having a 20 mm path length. The spectrophotometer was standardized in total transmission mode with a transmission cell filled with 10 wt % NH$_4$OH stock solution. The purpose of this standardization was to subtract the background color response of the cell and stock solution from the FDCA sample. The transmission of each sample was then measured to obtain the CIELAB value for b*.

Comparative Examples 1 and 2 demonstrate that the hydrogenation needs to be conducted at temperature where FDCA is sufficiently soluble in water. The dissolution temperature should be sufficiently high to obtain good dissolution of FDCA in the given solvent, otherwise b* and FFCA reduction by hydrogenation will be insufficient.

Examples 3 to 9 and 11 demonstrate that pFDCA with FFCA content of less than 10 ppm and a b* of less than 1 can be achieved via mild hydrogenation of crude FDCA.

Comparative Example 10 shows that at elevated hydrogenation temperatures, excessive ring hydrogenation occurs to form THFDCA in high quantities (appearing in the filtrate). The amount of THFDCA can be controlled at high hydrogenation temperatures by limiting the residence time and catalyst loading.

Comparative Example 12 shows that at higher hydrogenation partial pressure, excessive ring hydrogenation occurs to form THFDCA in high quantities (as appearing in the filtrate). The amount of THFDCA can be controlled at higher hydrogenation partial pressure by limiting the residence time and catalyst loading.

Comparative Example 13

This example illustrates the effect of severe hydrogenation on an FDCA composition. In this example, an large amount of catalyst metal was employed and under the hydrogenation conditions (temperature, hydrogen partial pressure, and residence time), most of the FDCA subjected to hydrogenation was converted to THFDCA.

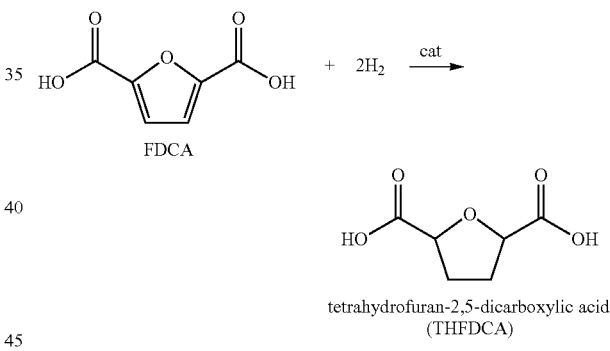

TABLE 1

| | crude FDCA solid | | | | | pFDCA solid[b] | | | |
|---|---|---|---|---|---|---|---|---|---|
| Example | FFCA (ppmw) | b* | mol ratio of FFCA to Pd[a] | Temp (° C.) | hydrogen partial pressure (psi) | reaction time (h) | FFCA (ppmw) | THFDCA (ppmw) | b* | % THFDCA yield in the filtrate |
| COMP 1 | 4000 | 44.12 | 15 | 100 | 285 | 3 | 480 | N.M. | 36.9 | 0.05 |
| COMP 2 | 4000 | 44.12 | 15 | 120 | 271 | 3 | 260 | N.M. | 21 | 0.06 |
| 3 | 10890 | 53.41 | 40 | 150 | 231 | 3 | <10 | 77 | 0.74 | 0.65 |
| 4 | 4000 | 44.12 | 26 | 150 | 231 | 3 | <10 | 43 | 0.75 | 0.64 |
| 5 | 4000 | 44.12 | 18 | 150 | 131 | 3 | <10 | 36 | 0.24 | 0.20 |
| 6 | 19320 | 61.84 | 71 | 170 | 185 | 3 | <10 | 18 | 0.98 | 0.36 |
| 7 | 4000 | 44.12 | 15 | 170 | 135 | 3 | <10 | 31 | 0.25 | 0.11 |
| 8 | 4000 | 44.12 | 15 | 170 | 85 | 3 | <10 | 23 | 0.34 | 0.11 |
| 9 | 19320 | 61.89 | 71 | 180 | 155 | 3 | <10 | N.M. | 0.96 | 0.14 |
| COMP 10 | 10890 | 53.41 | 40 | 200 | 75 | 3 | <10 | 12 | 0.24 | 2.59 |
| 11 | 10890 | 53.41 | 40 | 200 | 75 | 1 | <10 | 15 | 0.35 | <0.03 |
| COMP 12 | 4000 | 44.12 | 15 | 170 | 950 | 3 | <10 | 48 | 0.4 | 14.80 |

[a]0.5 wt % Pd on Carbon (CBA-300 SE 11233) was used.
[b]>99.95% pFDCA purity.
N.M = not measured A 300 mL titanium autoclave equipped with a catalyst basket was charged with FDCA (40.0 g, 256 mol) and 450.0 g of water. The catalyst basket was charged with 13.0 g of palladium/carbon catalyst (40% wet) containing 0.5 wt % palladium. The autoclave was sealed and heated to 170° C. while agitating the mixture. $H_2$ gas was introduced to attain 500 psi partial pressure. The total pressure was maintained from the surge tank during the reaction. The reaction continued for 4 h period of time and gas supply was stopped and the autoclave was cooled to room temperature and depressurized. The homogenous aqueous mixture was filtered to remove carbon black particles. The water was removed using rotavap to give a white solid. The white solid was oven dried at 110° C. under vacuum overnight. The product was analyzed by Gas Chromatography using BSTFA derivatization method and 91% (38.39 g) of THFDCA was obtained.

Comparative Example 14

This example illustrates the effect of FDCA hydrogenation under a severe reaction temperature.

A 300 mL titanium autoclave equipped with a catalyst basket was charged with FDCA (45.0 g, 256 mol) and 450.0 g of water. The catalyst basket was charged with 3.0 g of palladium/carbon catalyst (40% wet) containing 0.5 wt % palladium. The autoclave was sealed and heated to 250° C. while agitating the mixture. $H_2$ gas was introduced to attain 135 psi partial pressure. The total pressure was maintained from the surge tank during the reaction. The reaction continued for 3 h period of time and gas supply was stopped and the autoclave was cooled to room temperature and depressurized. The homogenous aqueous mixture was filtered to remove carbon black particles. The water was removed using rotavap to give only 2.1 g of intractable sticky solid. Though not bound by the theory most of FDCA or THFDCA underwent decarboxylation or hydrogenolysis at very high temperature catalyzed by palladium.

What we claim is:

1. A process for purifying a crude furan 2,5-dicarboxylic acid composition (cFDCA) comprising:
   a) providing a cFDCA composition comprising furan 2,5-dicarboxylic acid (FDCA) solids, 5-formyl furan-2-carboxylic acid (FFCA), and a oxidation solvent composition;
   b) combining a hydrogenation solvent composition with said FDCA solids and dissolving at least a portion of the FDCA solids to thereby produce a solvated FDCA (sFDCA) composition comprising dissolved FDCA, the hydrogenation solvent composition, and FFCA;
   c) in a hydrogenation reaction zone, hydrogenating the sFDCA at a temperature within a range of 130° C. to 225° C. by contacting the sFDCA composition with hydrogen in the presence of a hydrogenation catalyst to thereby hydrogenate FFCA and produce a furan 2,5-dicarboxylic acid composition (hFDCA) comprising a hydrogenated FFCA species, dissolved FDCA, and said hydrogenation solvent; and
   e) separating at least a portion of the dissolved FDCA from the hFDCA composition to obtain a product FDCA (pFDCA) composition.

2. The process of claim 1, wherein the cFDCA composition comprises at least 15 wt. % solids based on the weight of the cFDCA composition, wherein at least 85 wt. % of the solids is FDCA based on the weight of the solids; and FFCA.

3. The process of claim 2, wherein the cFDCA composition comprises at least 28 wt. % solids based on the weight of the cFDCA composition, wherein at least 90 wt. % of the solids is FDCA based on the weight of the solids; and at least 0.2 wt. % FFCA.

4. The process of claim 2, wherein the cFDCA composition comprises 2,5 diformylfuran in an amount of 0 wt % to about 0.2 wt %; levulinic acid in an amount ranging from 0 wt % to 0.5 wt %; succinic acid in an amount ranging from 0 wt % to 0.5 wt %; acetoxyacetic acid in an amount ranging from 0 wt % to 0.5 wt %, and a cumulative amount of by-products other than FFCA present in an amount ranging from greater than 0 wt. % and up to 20 wt. %, in each case based on the weight of cFDCA composition.

5. The process of claim 2, wherein the cFDCA composition has a b* of at least 5.

6. The process of claim 1, wherein the amount of FFCA by weight present in the cFDCA composition relative to FFCA present in the pFDCA is reduced by a factor of at least 100×.

7. The process of claim 6, wherein the reduction of FFCA is by a factor of at least 500×.

8. The process of claim 1, wherein the cFDCA composition is fed to an evaporator to remove at least a portion of the oxidation solvent from cFDCA composition to produce a concentrated slurry.

9. The process of claim 8, wherein the concentrated slurry is fed to a solid/liquid separation zone to remove at least a portion of the oxidation solvent as a mother liquor to produce a wet cake, and said wet cake is washed to produce a washed cFDCA cake.

10. The process of claim 9, wherein the washed cFDCA cake is fed to a dissolution zone for dissolving the washed cFDCA cake in a hydrogenation solvent composition.

11. The process of claim 1, wherein the cFDCA composition is fed to a solid/liquid separation zone to separate the oxidation solvent from the cFDCA composition.

12. The process of claim 11, wherein the FDCA solids are, after or simultaneous with separation of the oxidation solvent, combined with a hydrogenation solvent to dissolve at least 98% of the FDCA solids and thereby produce a solvated FDCA composition.

13. The process of claim 1, wherein the FDCA solids in step b are dissolved in the hydrogenation solvent at a temperature within a range of 130° C. to 200° C.

14. The process of claim 1, wherein the hydrogenation solvent composition comprises at least 90 wt. % water based on the weight of hydrogenation solvent composition.

15. The process of claim 1, wherein the sFDCA composition comprises:
   a) less than 1 wt. % solids;
   b) dissolved FDCA in an amount of at least 7 wt. %; and
   c) a hydrogenation solvent in an amount of at least 50 wt. %;
   d) FFCA in an amount of at least greater than 0 wt. %;
in each case based on the weight of the sFDCA composition.

16. The process of claim 1, wherein the sFDCA composition is fed to the hydrogenation reactor at a temperature within a range of 135° C.-200° C.

17. The process of claim 1, wherein hydrogenation is conducted at a temperature within a range of 130° C. to less than 200° C.

18. The process of claim 1, wherein the partial pressure of hydrogen is within a range of 50 psi to 500 psi.

19. The process of claim 1, wherein hydrogenation is conducted under conditions effective to produce a pFDCA composition containing less than 500 ppm tetrahydrofuran dicarboxylic acid ("THFDCA"), based on the weight of FDCA solids in the pFDCA composition.

20. The process of claim 1, wherein the hFDCA composition is crystallized.

21. The process of claim 1, wherein the pFDCA composition comprises:
   a) solids, wherein at least 98 wt. % of the solids are FDCA;
   b) a b* of at least zero and less than 4;
   c) FFCA in an amount of less than 200 ppm; and
   d) tetrahydrofuran dicarboxylic acid ("THFDCA") present in an amount ranging from 0 to 0.5 wt. %;
in each case based on the weight of the solids.

22. The process of claim 21, wherein the pFDCA composition comprises at least 98 wt. % solids.

23. The process according to any one of claims 1-22, wherein the hydrogenation solvent comprises at least 90 wt. % water.

24. The process of any one of claim 1-22, wherein hydrogenation is conducted under a hydrogen partial pressure within a range of 10 psi to 900 psi and a total pressure within the hydrogenation reaction zone within a range of 35 psig to less than 950 psig.

25. The process of claim 24, wherein the total pressure is within a range of 50 psig to 930 psig.

26. The process of claim 24, wherein the hydrogen partial pressure is within a range of 20 psi to 400 psi.

27. The process of claim 1, wherein the moles of FFCA fed into the hydrogenation reactor per hour to the moles of total catalyst metal(s) employed in the hydrogenation reactor is at least 0.1 hr$^{-1}$:1.

28. The process according to any one of claims 1-22, wherein the yield of FDCA, on a solids basis and measured in the pFDCA composition, is at least 80%.

29. The process according to any one of claims 1-22, wherein the process is operated to produce at least 20,000 kg/day of pFDCA on a solids basis, on a 24 hour basis over the course of any three months.

* * * * *